(12) United States Patent
Thomas et al.

(10) Patent No.: US 9,707,316 B2
(45) Date of Patent: Jul. 18, 2017

(54) CROSSLINKED POLYMERS INCLUDING ONE OR MORE ANTIOXIDANTS, METHODS FOR MAKING SAME AND METHODS FOR SELECTING ANTIOXIDANTS

(71) Applicant: Zimmer, Inc., Warsaw, IN (US)

(72) Inventors: Brian H. Thomas, Auburndale, FL (US); Dean M. Acker, Naples, FL (US); Ray Gsell, Hubert, NC (US); Norman Stark, Winterthur (CH)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 15/149,583

(22) Filed: May 9, 2016

(65) Prior Publication Data

US 2016/0250381 A1  Sep. 1, 2016

Related U.S. Application Data

(62) Division of application No. 13/991,719, filed as application No. PCT/US2011/063294 on Dec. 5, 2011, now Pat. No. 9,370,602.

(60) Provisional application No. 61/420,246, filed on Dec. 6, 2010.

(51) Int. Cl.
| | | |
|---|---|---|
| C08F 2/46 | (2006.01) | |
| C08F 2/50 | (2006.01) | |
| C08G 61/04 | (2006.01) | |
| A61L 27/16 | (2006.01) | |
| A61L 27/50 | (2006.01) | |

(52) U.S. Cl.
CPC .............. *A61L 27/16* (2013.01); *A61L 27/50* (2013.01); *A61L 27/505* (2013.01)

(58) Field of Classification Search
CPC ........ A61L 27/16; A61L 27/50; A61L 27/505; C08L 23/06
USPC ............... 522/75, 74, 71, 189, 184, 1; 520/1
See application file for complete search history.

(56) References Cited

U.S. PATENT DOCUMENTS

| | | | |
|---|---|---|---|
| 9,370,602 B2 | 6/2016 | Thomas et al. | |
| 2002/0040081 A1 | 4/2002 | Stein et al. | |
| 2010/0249945 A1* | 9/2010 | Yakimicki | A61L 27/16 623/23.59 |
| 2012/0046380 A1* | 2/2012 | Morrison | A61F 2/30767 522/75 |
| 2014/0005293 A1 | 1/2014 | Thomas et al. | |

FOREIGN PATENT DOCUMENTS

| | | | |
|---|---|---|---|
| WO | WO-2008006890 A2 | 1/2008 | |
| WO | WO-2009138103 A1 | 11/2009 | |
| WO | 2010-129514 | * 11/2010 | |
| WO | WO-2010129514 A2 | 11/2010 | |

OTHER PUBLICATIONS

"U.S. Appl. No. 13/991,719, Non Final Office Action mailed Oct. 8, 2015", 9 pgs.
"U.S. Appl. No. 13/991,719, Notice of Allowance mailed Feb. 29, 2016", 10 pgs.
"U.S. Appl. No. 13/991,719, Preliminary Amendment mailed Jun. 5, 2013", 4 pgs.
"U.S. Appl. No. 13/991,719, Preliminary Amendment mailed Jun. 19, 2013", 6 pgs.
"U.S. Appl. No. 13/991,719, Response filed Jan. 6, 2015 to Non Final Office Action mailed Oct. 8, 2015", 10 pgs.
"U.S. Appl. No. 13/991,719, Response filed Sep. 21, 2015 to Restriction Requirement mailed Aug. 13, 2015", 9 pgs.
"U.S. Appl. No. 13/991,719, Restriction Requirement mailed Aug. 13, 2015", 9 pgs.
"European Application Serial No. 11806015.1, Communication Pursuant to Article 94(3) EPC mailed Feb. 1, 2016", 5 pgs.
"European Application Serial No. 11806015.1, Examination Notification Art. 94(3) mailed Jun. 17, 2014", 6 pgs.
"European Application Serial No. 11806015.1, Response filed Feb. 24, 2014 to Office Action mailed Aug. 14, 2013", 13 pgs.
"European Application Serial No. 11806015.1, Response filed Oct. 27, 2014 to Examination Notification Art. 94(3) mailed Jun. 17, 2014", 11 pgs.
"International Application Serial No. PCT/US2011/063294, International Preliminary Report on Patentability mailed Jun. 20, 2013", 6 pgs.
"International Application Serial No. PCT/US2011/063294, International Search Report mailed Mar. 9, 2012", 3 pgs.
"International Application Serial No. PCT/US2011/063294, Written Opinion mailed Mar. 9, 2012", 4 pgs.
"European Application Serial No. 11806015.1, Response filed Jun. 13, 2016 to Communication Pursuant to Article 94(3) EPC mailed Feb. 1, 2016", 12 pgs.

* cited by examiner

*Primary Examiner* — Jessica A Whiteley
(74) *Attorney, Agent, or Firm* — Schwegman Lundberg & Woessner, P.A.

(57) ABSTRACT

Polymer compositions having one or more antioxidants providing high crosslink density and improved oxidation resistance to the polymer composition and methods for making same. Such polymer compositions can be used to make orthopedic implants.

20 Claims, 15 Drawing Sheets

CROSSLINKED POLYMERS INCLUDING ONE OR MORE ANTIOXIDANTS, METHODS FOR MAKING SAME AND METHODS FOR SELECTING ANTIOXIDANTS

CROSS-REFERENCE TO RELATED APPLICATION

This application is a divisional of U.S. patent application Ser. No. 13/991,719, filed on Sep. 18, 2013, which is a U.S. National Stage Filing under 35 U.S.C. §371 of International Patent Application Ser. No. PCT/US2011/063294, filed on Dec. 5, 2011, published on Jun. 14, 2012 as WO 2012/078514 A1, which claims the benefit of priority under 35 U.S.C §119(e) of U.S. Provisional Application Ser. No. 61/420,246 filed on Dec. 6, 2010, the benefit of priority of each of which is claimed hereby and the entirety of each of which is incorporated herein by reference.

TECHNICAL FIELD

The present disclosure relates to crosslinked polymer compositions including a polymer and one or more antioxidants for improving the oxidative resistance of the polymer compositions, and methods for making same. In particular, the disclosure is directed to polymer compositions having a high crosslink density and enhanced oxidative resistance by including one or more antioxidants, and criteria for selecting antioxidant and antioxidant blends providing high crosslink density and enhanced oxidative resistance to polymer compositions.

BACKGROUND

Crosslinked polymers such as crosslinked polyethylene (PE) and more particularly ultrahigh molecular weight polyethylene (UHMWPE) have found extensive use in implant devices such hip, knee and shoulder implants. Such implants typically include a ceramic or metallic piece which articulates against a UHMWPE article or bearing surface. UHMWPE has been the polymer of choice for its high strength, biocompatibility, and wear resistance. Crosslinking the UHMWPE has been found to improve wear resistance but typically at the cost of diminished oxidative resistance particularly when no post processing of the crosslinked polymer such as heat treatment including annealing and remelting is crosslinking is typically accomplished by exposing the UHMWPE to gamma, beta or x-ray irradiation which causes scissions of the C—C and C—H bonds and creates free radical polymer molecules. These free radicals can undergo recombination and rearrangement reactions to form crosslinks. However, some free radicals may remain in the polymer material following irradiation, which could potentially combine with oxygen, nitric oxide, hydrogen peroxide, hypochlorite anion, and nitrite whether present in the outer environment or in the body to cause oxidation of the polymer material.

Several techniques have been developed in order to reduce the amount or number of free radicals created by crosslinking. One method of reducing the free radicals due to crosslinking has been to expose the crosslinked polymer heat treatments such as annealing or melt techniques that usually raise the temperature of the crosslinked polymer composition to slightly below, at or slightly above the melting point of the polymer. This improves the mobility of the free radicals within the polymer and allows some of the free radicals to form additional crosslinks or other bonds thereby quenching the free radicals. Even with such heating methods, some free radicals persist in the polymer. Another approach has been to incorporate an antioxidant into the polymer whether by blending the antioxidant with unconsolidated UHMWPE raw material or through infusing or doping after the UHMWPE raw material has been consolidated. Using both an antioxidant and annealing or melt technique is yet another approach to improving the oxidation resistance of the polymer, as disclosed for example in U.S. Patent Publication Nos. 20070059334 published Mar. 15, 2007 and 20100029858 published Feb. 4, 2010.

Melt techniques and antioxidant incorporation does impose a cost however. Melt techniques can result in diminishment of the crystalline structure of the polymer which can result in some loss of desirable mechanical properties. Incorporation of antioxidants can result in reduced amount of crosslinking per unit of radiation as the antioxidant quenches the free radicals before they can form crosslinks. To compensate for the reduction of crosslinking due to antioxidant scavenging of the free radical, higher radiation doses can be used. However, using higher doses can detrimentally impact the structural integrity of the polymer by causing excessive bond scissions. This is one reason why some choose to consolidate and irradiate the polymer prior to doping with an antioxidant.

The preferred antioxidant for use with implantable polymeric articles is vitamin E or alpha tocopherol due to its biocompatibility and acceptable scavenging of free radicals. Other antioxidants may also be suitable for use with implantable polymeric articles whether alone or in combination which allow the polymer to achieve higher crosslink density per unit of radiation and/or provide acceptable and even improved oxidation resistance.

SUMMARY

The present disclosure is directed to polymer compositions and having one or more antioxidants providing high crosslink density and improved oxidation resistance to the polymer composition and methods for making same. The disclosure also provides methods for selecting antioxidants providing desirable properties to the polymer composition. In one embodiment, Oxidation Induction Time (OIT) can be used to select the antioxidant and antioxidant blend. In another embodiment, measurements of OIT and Oxidation Index rate (OI-rate) can be used to select the one or more antioxidants.

In one aspect, the present disclosure is directed to an orthopedic implant which includes a consolidated and crosslinked UHMWPE blend. The UHMWPE blend has a homogeneous blend of UHMWPE resin, a first antioxidant and a second antioxidant and wherein the combined concentration of the first and second antioxidants prior to crosslinking is from about 0.05% to about 5% by weight of the UHMWPE blend.

In another aspect, the present disclosure is directed to an orthopedic implant which includes a consolidated and crosslinked UHMWPE blend and the UHMWPE blend has a homogeneous blend of UHMWPE resin, a first antioxidant and a second antioxidant.

In still another aspect, the present disclosure is directed to an orthopedic implant which includes a consolidated and irradiated blend of UHMWPE, and first and second antioxidants wherein the starting concentration of the combination of first and second antioxidants is from about 0.05% to about 5% by weight of the blend.

In yet another aspect, the present disclosure is directed to an orthopedic implant which includes a homogenous blend of UHMWPE and two antioxidants present at a combined concentration of from about 0.05% to about 5% by weight of the blend wherein the blend is subsequently consolidated and crosslinked.

In still another aspect, the present disclosure is directed to an orthopedic implant which includes a consolidated and crosslinked article, the article formed by the process of (a) combining UHMWPE, a first antioxidant and a second antioxidant to form a UHMWPE blend wherein the combined concentration of the first and second antioxidants is from about 0.05% to about 5% by weight; (b) consolidating the homogenous UHMWPE blend; and (c) irradiating the consolidated homogenous UHMWPE blend to crosslink the consolidated homogenous UHMWPE blend.

In yet another aspect, the present disclosure is directed to an orthopedic implant which includes a consolidated and crosslinked homogenous blend of UHMWPE, a first antioxidant and a second antioxidant wherein the combined concentration of the first and second antioxidants is effective to produce an oxidation index and crosslinking performance factor greater than 2500 wherein the performance factor is calculated by the product of the crosslink density and the inverse of the oxidation index rate.

In still another aspect, the present disclosure is directed to an orthopedic implant which includes a consolidated and crosslinked homogenous blend of UHMWPE, a first antioxidant and a second antioxidant wherein the combined concentration of the first and second antioxidant is effective to produce an oxidation induction time and crosslinking performance factor greater than 1.5 wherein the performance factor is calculated by the product of the crosslink density and the oxidation induction time as measured by the offset method.

In yet another aspect, the present disclosure is directed to an orthopedic implant which includes a consolidated and crosslinked homogenous blend of UHMWPE, a first antioxidant and a second antioxidant wherein the combined concentration of the first and second antioxidants is from about 0.05% to about 0.2% by weight of the consolidated and crosslinked homogenous blend. In still another aspect, the present disclosure is directed to a method of making an implant. The method includes the steps of mixing UHMWPE resin with a first antioxidant and a second antioxidant to obtain a homogeneous blend; consolidating the blend; and irradiating the consolidated blend to crosslink the consolidated blend.

BRIEF DESCRIPTION OF THE DRAWINGS

In the following detailed description, reference will frequently be made to the following Figures in which.

DETAILED DESCRIPTION

Figure 1:
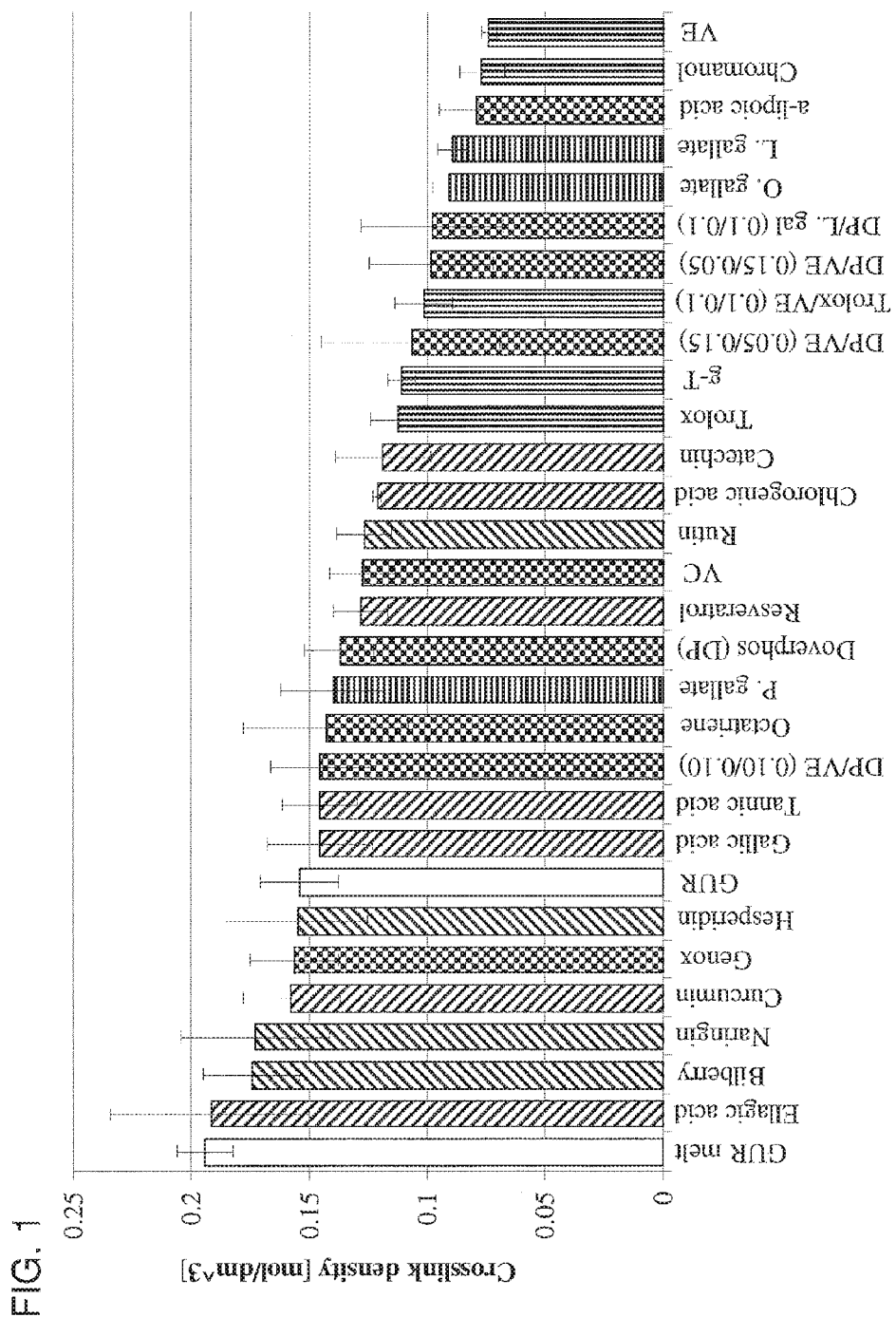
FIG. 1 shows a graph of crosslink density values of samples including a blend of UHMWPE and a variety of one or more antioxidants.

The disclosed methods, systems, compositions and polymers are merely exemplary of the inventions disclosed herein, which may be embodied in various forms, and specific details disclosed herein are not to be interpreted as limiting, but merely as a basis for the claims and as a representative basis for teaching one skilled in the art to variously employ the present approach in virtually any appropriate manner.

Polymeric materials have seen wide use in medical devices such as implants and more particularly orthopedic implants. A commonly used polymer for such applications is ultrahigh molecular weight polyethylene (UHMWPE) due to its biocompatibility and superior mechanical properties. The UHMWPE is typically provided as a resin in powder or small particle form. Examples of powdered or particle UHMWPE are GUR 1020 and GUR 1050 powder from Ticona having North American headquarters in Florence, Ky. The UHMWPE can be consolidated using known techniques such as compression and/or consolidation techniques include, for example, compression molding, direct compression molding, hot isostatic pressing, extrusion, high pressure crystallization, injection molding, net shape molding, monoblock formation, melt spinning, blow molding, solution spinning, sintering or other conventional methods of compressing and/or consolidating UHMWPE to form either the finished article or end product, or a preform which is defined as a substrate requiring additional processing to produce the end product. Preforms are typically consolidated blocks, sheets or rods of the UHMWPE material or UHMWPE blend which can include additives as discussed further below. These preforms can be further processed or manufactured by milling, machining, drilling, cutting, assembling with other components, and/or other manufacturing or pre-manufacturing steps conventionally employed to produce the end product such as an orthopedic implant.

One or more antioxidants can be combined with the UHMWPE powder using a variety of methods which can be characterized by whether the antioxidant is added prior to consolidation (blending) or after consolidation (doping). Methods of incorporating antioxidants with the polymer prior to consolidation can include physical mixing, mixing with the aid of a solvent, mixing with the aid of a solvent (e.g. $CO_2$) under supercritical temperature and pressure conditions, and ultrasonic mixing. Suitable mixing processes of these types are also described, for example, in U.S. Pat. Nos. 6,448,315 and 6,277,390, the disclosures of which are hereby incorporated by reference. Where the antioxidant is in solid form it can be added directly to the polymer powder and mixed in a dry mixer until a substantial uniform mixture is obtained to create a polymer blend. In one embodiment, the antioxidant or blend of antioxidants is dissolved in a solvent such as ethanol or isopropyl alcohol and is added drop-wise to a powdered UHMWPE material while mixing using a conventional dry mixer until a substantial uniform mixture is obtained. The solvent can then be removed via a vacuum dryer, fluidized drying bed, or similar apparatus to produce a UHMWPE blend.

Methods of incorporating antioxidants with the polymer after consolidation can include doping methods where the consolidated preform or end product can be exposed to the antioxidant or a solvent solution including the antioxidant under heat and/or pressure. Crosslinking can occur prior to or after the antioxidant doping. Such methods are described for example in WO2004/064618 published Aug. 5, 2004 by Muratoglu et al.

Prior to and/or after processing the implant as reported above, the preform of UHMWPE material, UHMWPE blend or end product can be crosslinked by exposure to radiation at a specified radiation dose and at a specified dose rate. Typically the radiation dose and/or dose rate can be greater than those required for irradiative sterilization such as using gamma, beta (electron beam or e-beam) or xray radiation. The dosage of radiation can be from about 25 to about 1000 kiloGrey. In one embodiment, electron beam radiation is utilized for crosslinking at a dose of at least about 25 kiloGrey up to about 500 kiloGrey, more particularly at least about 80 kiloGrey up to about 400 kiloGrey, even more particularly at least about 95 kiloGrey up to about 300 kiloGrey. In another embodiment, a dose of between about 100 kiloGrey to about 250 kiloGrey is applied. The dose rate selected can depend on the form of radiation used. For example, gamma radiation can be provided at a does rate of from about 0.5 to about 10 kiloGrey per hour whereas e-beam radiation can be provided at from about 1 to about 2000 megaGrey per hour. In another embodiment, the UHMWPE blend may be exposed to e-beam radiation at a dose rate of at least 1 MegaGrey per hour, more particularly at least about 15 MegaGrey per hour, and even more particularly about 18 MegaGrey per hour. In certain embodiments, the desired radiation dose may be achieved in a single exposure step at a high dose rate. In other embodiments, a series of lower dose rate irradiation steps may be employed to obtain a desired dose of radiation.

Electron beam radiation exposure may be performed using conventionally available electron beam accelerators. One commercial source for such an accelerator is IBA Technologies Group, Belgium. Suitable accelerators may produce an electron beam energy between about 2 and about 50 MeV, more particularly about 10 MeV, and are generally capable of accomplishing one or more of the radiation doses and/or dosage rates reported herein. Electron beam exposure may be carried out in a generally inert atmosphere, including for example, an argon, nitrogen, vacuum, or oxygen scavenger atmosphere. Exposure may also be carried out in air under ambient conditions according to one embodiment. In one embodiment the irradiation is carried out under a nitrogen atmosphere and subsequently stored under vacuum in light-opaque packaging in 0° C. freezers until further processing.

Prior to, during and/or after electron beam irradiation, the consolidated UHMWPE blend or UHMWPE and antioxidant may be subjected to one or more temperature treatments. In one embodiment, the UHMWPE blend may be heated above room temperature (between 20° C. and 30° C.) prior to irradiation wherein the preheated consolidated UHMWPE blend is then irradiated. For example, the consolidated UHMWPE blend may be heated to between about 40° C. to below the melting point of the UHMWPE blend. In other embodiments, the consolidated UHMWPE blend may be heated prior to irradiation to between about 40° C. to about 140° C., between about 50° C. to about 100° C., between about 50 C. and 65° C. or between about 120° C. and 130° C. Such heat treatments prior to irradiation are described in detail in U.S. Pat. Pub. No. 2007059334, published Mar. 15, 2007 to Rufner et al., which is hereby incorporated by reference. In another embodiment, the UHMWPE blend may remain at room temperature or may even be cooled below room temperature, such as for example, below a glass transition temperature of the UHMWP. After irradiation, the crosslinked preform or end product may be annealed at a temperature of up to about 200° C. for up to about 72 hours, more particularly at about 150° C. for about 5 hours. In other embodiments, the crosslinked preform or consolidated UHMWPE blend may be annealed at a temperature below the melting point of the UHMWPE. Alternatively or additionally, the crosslinked UHMWPE and antioxidant preform may be subjected to the mechanical annealing processes reported in U.S. Pat. No. 6,853,772 to Muratoglu, which is hereby incorporated by reference. In one embodiment, no pre- or post-irradiation temperature and/or annealing treatments are performed.

In another embodiment, the temperature of the consolidated UHMWPE blend is maintained below the melting temperature of the polymer (e.g., about 140° C. for UHMWPE) during irradiative crosslinking procedure. This may require cooling to prevent heating caused by the irradiation treatment, varying the strength or intensity of the irradiation treatment and/or may even require conducting the irradiation treatments at paused intervals.

The preform may be further processed or manufactured by milling, machining, drilling, cutting, assembling with other components, and/or other manufacturing or pre-manufacturing steps conventionally employed to manufacture an end product from the UHMWPE blend. End products can be implants such as an orthopedic implant. As part of the implant manufacturing process, additional components may be combined with the preform at any time during the manufacturing process. In one embodiment, tribological components such as metal and/or ceramic articulating components and/or preassembled bipolar components may be joined with the preform. In other embodiments, metal backing (e.g. plates or shields) may be added. In further embodiments, surface components such a trabecular metal, fiber metal, beats, Sulmesh® coating, meshes, cancellous titanium, and/or metal or polymer coatings may be added to or joined with the preform. Still further, radiomarkers or radiopacifiers such as tantalum, steel and/or titanium balls, wires, bolts or pegs may be added. Further yet, locking features such as rings, bolts, pegs, snaps and/or cements/adhesives may be added. These additional components may be used to form sandwich implant designs, radiomarked implants, metal-backed implants to prevent direct bone contact, functional growth surfaces, and/or implants with locking features.

A variety of implants, and in particular endoprosthetic joint replacements, may be prepared by employing the methods reported herein. Examples of such implants include artificial hips and knees, cups or liners for artificial hips and knees, spinal replacement disks, artificial shoulder, elbow, feet, ankle and finger joints, mandibles, and bearings of artificial hearts.

After manufacturing of the implant has been completed, the implant may be packaged and sterilized prior to distribution. Packaging is generally carried out using either gas permeable packaging or barrier packaging utilizing a reduced oxygen atmosphere. Because the presence of one or more antioxidants in the UHMWPE inhibits the oxidation cycle, conventional gas permeable packing may be suitable for embodiments of the present invention. Barrier packaging with an inert gas backfill (e.g. argon, nitrogen, oxygen scavenger) is also suitable.

Sterilization may be accomplished either by radiation exposure during crosslinking of the UHMWPE blend, or as part of a separate processing step. A number of conventional sterilization techniques exist including gas plasma sterilization, ethylene oxide sterilization, gamma radiation and e-beam radiation sterilization. In one embodiment crosslinking can be carried out prior to packaging either in a separate step from the crosslinking step or concurrently with crosslinking since if radiation is used such as e-beam radiation the radiation may be sufficient to result in sterilization. When sterilization occurs in a separate step any of the above sterilization techniques can be used.

In another embodiment sterilization occurs after packaging again either in a separate step from the crosslinking step or concurrently with crosslinking. In yet another embodiment sterilization and crosslinking can be carried out by e-beam irradiation in a single step after packaging the implant.

As noted above, crosslinking can have positive effects on certain mechanical properties of the consolidated UHMWPE such as wear rate which can outweigh less desirable effects on other mechanical properties if any. Improved wear rate may be one of the more desirable properties of implants which are subject to friction such as articulating orthopedic implants.

Crosslinking can also render the UHMWPE more susceptible to oxidation as some of the free radicals created during crosslinking do not form crosslinks but rather persist in the polymer matrix. As shown in the EXAMPLE section below, consolidated UHMWPE irradiated at 100 kGrey oxidized faster than the similarly irradiated GUR melt which underwent a post irradiation heat processing as shown by OI-rate in FIG. 12.

The free radicals can react in the presence of oxygen to form peroxyl radicals. These free radicals and peroxyl radicals may react with the polyethylene backbone and with each other to form oxidative degradation products and additional radical species. This cycle of oxidation product and radical species formation may occur over several years (both prior to and after implantation) as oxidation levels in the implant increase. It has been suggested that in vivo oxidation of a crosslinked UHWMPE can occur through absorption of biological fluids such as lipids and squaline that in turn can generate hydroperoxides leading to oxidation of the polymer.

The incorporation of one or more antioxidants can address these oxidation mechanisms. Some antioxidants and antioxidant blends can perform better than others in terms of providing oxidation resistance. Accordingly, the degree of oxidation resistance offered by a particular antioxidant or antioxidant blend can be a factor to consider in selecting the antioxidant or antioxidant blend.

Adding antioxidants can also result in other effects on the UHMWPE. For example, adding one or more antioxidants prior to crosslinking such as in embodiments in which the antioxidant is blended with the unconsolidated UHMWPE powder and then consolidated and exposed to crosslinking irradiation can lessen the degree of crosslinking due to the antioxidants quenching the free radicals. Hence, the effect on the amount of crosslinking, which can be expressed as crosslink density, can be another factor in selecting an antioxidant or antioxidant blend.

Including additives such as antioxidants in a UHMWPE material can also affect mechanical properties. Depending on the final end product some mechanical properties can be more desirable than others. Accordingly, the effect on mechanical properties of interest can be yet another factor in selecting an antioxidant or antioxidant blend.

Should the UHMWPE material be an implantable device, biocompatibility of the antioxidant and antioxidant byproducts can be another issue to consider.

The number of antioxidants that may be suitable for use in implantable articles is large. Antioxidants can be grouped or characterized in many ways such as by chemical type or structure. Antioxidants can also be characterized by their effectiveness in addressing particular free radical species. For example primary) (1° antioxidants are known or suspected to react directly with free peroxy radicals (ROO*) while secondary (2°) antioxidants such as Doverphos® are known or suspected to react with hydroperoxides to yield non-reactive species.

In one embodiment, UHMWPE can be blended with any of the antioxidant or antioxidant blends shown below in Table 1.

TABLE 1

| AO Group | Key | Formulation [supplier] | Type | AO structure |
|---|---|---|---|---|
| Control (No AO added) | | GUR 1050 (GUR) | N/A | N/A |
| | | GUR 1050 remelted (GUR melt) | N/A | N/A |
| VE-like | | Vitamin E (VE, α-tocopherol) [DSM] | 1° | (structure of α-tocopherol) |
| | | Gamma-tocopherol (γ-T) [Sigma] | | (structure of γ-tocopherol) |
| | | Trolox [Acros] | 1° | (structure of Trolox) |
| | | Trolox/VE (0.1%/0.1%) [blend] | 1° | Blend |
| | | 2,2,5,7,8-penta-methyl-6-chromanol (Chromnol) [Aldrich] | 1° | (structure of Chromanol) |
| Gallate | | Lauryl Gallate (L. gallate) [Acros] | 1° | (structure of lauryl gallate) |
| | | Octyl Gallate (O. gallate) [Sigma] | 1° | (structure of octyl gallate) |
| | | Propyl Gallate (P. gallate) [Sigma] | 1° | (structure of propyl gallate) |

TABLE 1-continued
| | | | |
|---|---|---|---|
| Phenolic | Curcumin [Acros] | 1° | 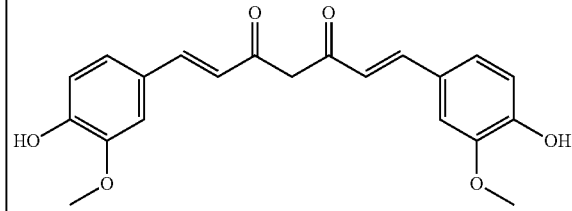 |
| | Resveratrol [Genceutic Laboratories, Cedar Grove, NJ] | 1° | |
| | Catechin [Cayman Chemical, Ann Arbor, MI] | 1° | 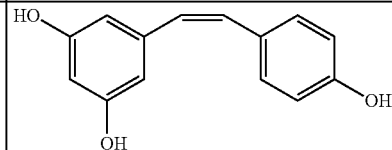 |
| | Chlorogenic acid [MP Biomedical, LLC., Solon, Ohio] | 1° | 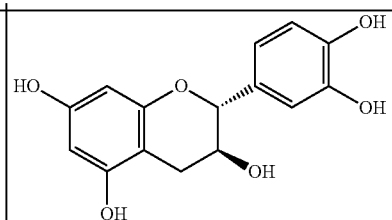 |
| | Tannic acid [Sigma] | 1° | 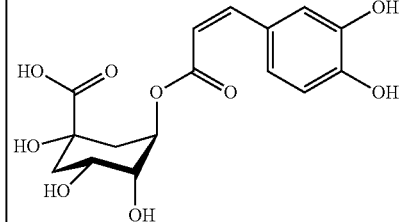 |

TABLE 1-continued
| | | | |
|---|---|---|---|
| | Gallic acid [Sigma] | 1° |  |
| | Ellagic acid [Sigma] | 1° | 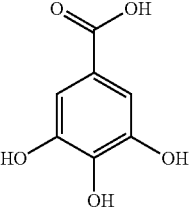 |
| Glycoside | Bilberry [Vitamin Shoppe, North Bergen, NJ] | 1° | 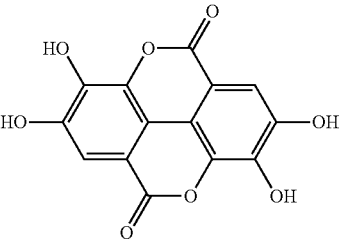 |
| | Rutin [Sigma] | 1° |  |

TABLE 1-continued
| | | | |
|---|---|---|---|
| | Hesperidin [Sigma] | 1° | 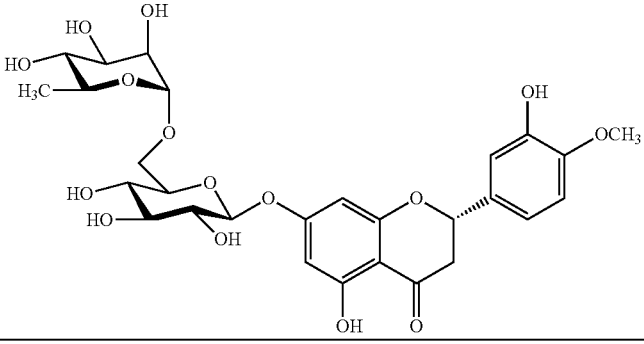 |
| | Naringin [Sigma] | 1° | 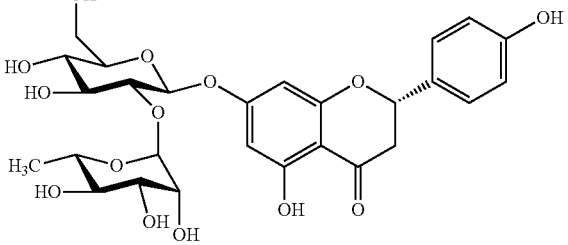 |
| | | | | |
|---|---|---|---|---|
| Other | Doverphos (DP) [Dover Chemical Corporation] | 2° | 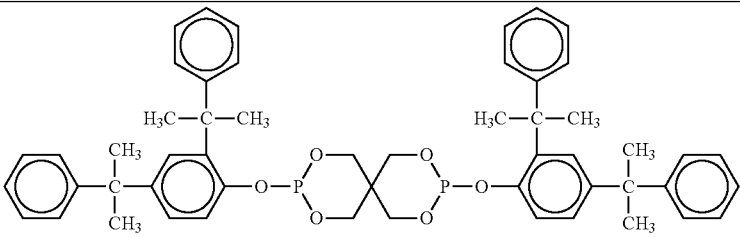 | |
| | DP/VE (0.05/0.15) [blend] | 1°/2° | Blend | |
| | DP/VE (0.10/0.10) [blend] | 1°/2° | Blend | |
| | DP/VE (0.15/0.05) [blend] | 1°/2° | Blend | |
| | DP/VE (0.20/0.20) [blend] | 1°/2° | Blend | |
| | DP/L. gal (0.1/0.1) [blend] | 1°/2° | Blend | |
| | a-lipoic acid [Sigma] | 2° | 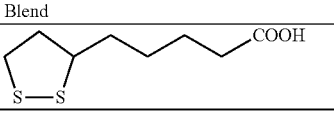 | |
| | Genox [Chemtura Corp, Morgantown, WV] | 1° | 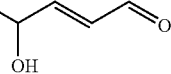 | |

TABLE 1-continued

| | | | |
|---|---|---|---|
| | Vitamin C (VC) [Aldrich] | 1° | 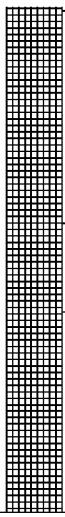 |
| | 2,6-dimethyl-2,4,6-octratriene (Octatriene) [Aldrich] | 1° | 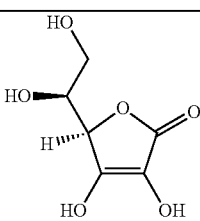 |
| | Irganox 1010 [Ciba] | 1° | 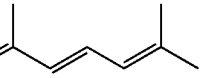 |

The one or more antioxidants can be dissolved in a solvent and added to UHMWPE powder and combined in a mixer to form a homogeneous UHMWPE blend. The antioxidant can be added at a concentration of from about 0.01 to about 5% by weight of the UHMWPE blend. Where a mixture of two or more antioxidants is added each of the constituent antioxidants can also be included at a concentration of from about 0.01 to about 5% by weight of the UHMWPE and antioxidant blend or the combined or total concentration of the two or more antioxidants can be from about 0.01% to about 5% of the UHMWPE blend. In one embodiment the one or more antioxidants can be added at a total or combined concentration of from about 0.05 to about 2% by weight of the UHMWPE blend. In another embodiment the one or more antioxidant can be added at a combined concentration of from about 0.1 to about 0.5% by weight of the UHMWPE blend. In yet another embodiment the one or more antioxidant can be added at a combined concentration of from about 0.15 to about 0.3% by weight of the UHMWPEblend. In still another embodiment the one or more antioxidant, can be added at a combined concentration of about 0.2% by weight of the UHMWPE blend. In another embodiment each of two antioxidants can be added at a concentration of from about 0.05 to about 0.2% by weight of the UHMWPE blend.

UHMWPE blends which include two antioxidants, the antioxidants can be included in selected concentration ratios. For example the concentration ratio of one antioxidant to another antioxidant can from about 10:1 to about 1:10 and optionally from about 5:1 to 1:5. More specifically the concentration ratio of first and second antioxidants can be from about 4:1 to about 1:4 and even more specifically from about 1:3 to about 3:1.

It is understood that the concentration of one or more antioxidants used to produce the UHMWPE blend are initial concentration levels, i.e. the concentration present prior to consolidation, irradiation, heat treatments and further processing. As the UHMWPE blend undergoes further processing such as consolidation and crosslinking treatments, the concentration of the antioxidant or antioxidant combination may diminish or the antioxidant(s) may be chemically transformed. The antioxidant(s) may be diminished or transformed through multiple pathways such as by reacting with free radicals formed during crosslinking and/or by bonding or grafting to the polymer backbone, among other pathways. Accordingly, the initial concentration of the antioxidant compound(s) may not equal the concentration after consolidation, crosslinking irradiation and/or pre- or post-heating. An amount of antioxidant(s) effective to provide oxidation resistance remains as evidenced by testing described below. It is also likely, that antioxidant(s) grafted to the polymer backbone may also provide oxidation resistance.

The degree to which the concentration is reduced can depend on many variables such as the type of consolidation method used, the type of crosslinking irradiation used and the dosage and dose rate of irradiation used. The degree of temperature rise during consolidation, irradiation treatment and any pre- and post-irradiation heat treatments conducted on the consolidated UHMWPE blend can also affect the final concentration of the antioxidant or antioxidant combination in the final UHMWPE article or post processed preform.

The UHMWPE blend can then be consolidated using any the consolidation methods described above. In one embodiment, compression molding is used to form a preform. The preform can be irradiated to form crosslinks and then further processed by cutting, milling polishing or other process steps to form an implantable article as described above.

As discussed above, each of the antioxidant or antioxidant mixes can have a different affect on the crosslink density of the consolidated UHMWPE. As is known in the art, higher crosslink density correlates with improved wear resistance. In addition, the amount of radiation may also be factored in determinations of the ability of antioxidant or antioxidant mixes to permit higher crosslink densities. As is understood in the art, higher radiation doses can provide increased crosslink densities up to a point of diminishing returns as too high a radiation dose may detrimentally affect structural properties of the polymer and oxidation rate.

Each of the antioxidant or antioxidant mixes or combinations can also have different effectiveness in terms of providing oxidation resistance. In addition, each antioxidant can also have a different affect on individual mechanical properties. Test methods for measuring crosslink density (XLD), oxidation parameters and mechanical properties are available for providing an empirical basis for determining the effect of the additive on UHMWPE and antioxidant blends. Preferably, the antioxidant or antioxidant mixture used provides high crosslink density, extended oxidation resistance and acceptable mechanical properties.

Oxidation resistance can be measure in several ways. Two such methods can be Oxidation Induction Time (OIT) and Oxidation Index (OI). OIT can assess reaction with oxygen in terms of exothermic reaction in the melt state. In other words OIT provides a measure of the length of time to the onset of oxidation of the sample such as a consolidated UHMWPE and antioxidant blend. Accordingly, the greater the OIT value the better the oxidation resistance.

OI can measure generation of oxygen-containing functional groups in the solid state and is typically measured over time to establish an OI-rate. Measuring OI-rate in real-time is not feasible as oxidation of consolidated and irradiated UHMWPE can take many years, i.e. anywhere from 5-20 years, so accelerated aging methods can be used. OI values taken over time can be used to calculate a linear rate of oxidation (OI-rate) by linear regression of oxidation index as a function of time. Hence, the lower the value of OI-rate the better the oxidation resistance.

As shown by the Examples, OIT and OI-rate imply an inverse relationship suggesting that OIT may serve as an indicator of long-term oxidative stability. According to the Examples, it has been found that while OIT produces some false negative predictions for OI-rate, it does not produce false positives. That is, consolidated and irradiated UHMWPE and antioxidant blends that perform well in terms of OIT perform well in terms of OI-rate.

This OI-OIT trend may be predictive of oxidation resistance. It is noted that the relationship may be strongest at higher values of OIT. In terms of technique, accuracy issues with OIT calculations at very short times may not be as accurate as shown in the Example section below.

In one embodiment, one or more of OIT, OI-rate and crosslink density can be used to select higher performing antioxidants and antioxidant mixtures for use in UHMWPE materials. In one embodiment, crosslink density can be measured using swell ratio in accordance with ASTM F 2214-02, the OIT can be measured by differential scanning calorimetry in accordance with ASTM D 3895-98 (offset method) and Oxidation index (OI) can be measured by transmission Fourier-transform infrared spectroscopy in accordance with ASTM F 2102-01. A series of OI values can be obtained over time beginning with a measurement prior to subjecting the sample to an accelerated or simulated aging environment and then taking measurements at specified intervals of time while the sample is stored in a simulated or accelerated aging environment. The accelerated or simulated aging environment can consist of storage or exposure in a digital convection oven maintained at 80±2° C. in air and can use an accelerated aging factor (AAF) of 55.7 from the relationship in ASTM F 1980-99e1 (equation 1), standard values for Q10=2 and TRT=22° C., to simulate the equivalent of roughly one year of real-time aging for each week of simulated or accelerated aging. OI-rate can then be determined by calculating a linear rate of oxidation by linear regression of OI as a function of time.

In another embodiment, one or more of OIT, OI-rate and crosslink density can be used to select higher performing antioxidants and antioxidant mixtures for use in UHMWPE materials. In one embodiment, crosslink density can be measured using swell ratio in accordance with ASTM F 2214-02, the OIT can be measured by differential scanning calorimetry in accordance with ASTM D 3895-07 (tangential method) and Oxidation index (OI) can be measured by transmission Fourier-transform infrared spectroscopy in accordance with ASTM F 2102-01. A series of OI values can be obtained over time beginning with a measurement prior to subjecting the sample to an accelerated or simulated aging environment and then taking measurements at specified intervals of time while the sample is stored in a simulated or accelerated aging environment. The accelerated or simulated aging environment can consist of storage or exposure in a digital convection oven maintained at 80±2 C in air and can use an accelerated aging factor (AAF) of 55.7 from the relationship in ASTM F 1980-99e1 (equation 1), standard values for Q10=2 and TRT=22° C., to simulate the equivalent of roughly one year of real-time aging for each week of simulated or accelerated aging. OI-rate can then be determined by calculating a linear rate of oxidation by linear regression of OI as a function of time.

As discussed above crosslinking can improve the wear resistance of UHMWPE but can also expose the UHMWPE to increased oxidative degradation. The addition of vitamin E to UHMWPE has been used to combat or prevent oxidation which may occur in crosslinked UHMWPE. While the addition of vitamin E has helped to improve the oxidative resistance of UHMWPE, vitamin E can also reduce the degree of crosslinking by quenching or scavenging the free radicals which can form the crosslinks and thus possibly adversely impact wear resistance. In one embodiment an UHMWPE blend including UHMWPE and at least one antioxidant, preferably two antioxidants can have a crosslink density of greater than 0.075 mol/dm$^3$.

Since the addition of vitamin E can have both positive effects (improving oxidative stability) and negative effects (reducing the crosslink density) it would be advantageous to provide a method for rapidly differentiating antioxidants and UHMWPE blends which can provide increased crosslink density and therefore a increased wear resistance and increased oxidative stability without requiring long-term mechanical wear resistance and oxidation testing. In one embodiment a hybrid parameter referred to as a "Performance Factor" (PF) can be calculated. Two potential PF calculations can be utilized. The PF calculations can use crosslink density as an indicator of wear rate resistance and either OIT or 1/OI-rate as an indicator measure of oxidative stability. The PFs disclosed herein can effectively ratio crosslink density to oxidization rate, therefore a low crosslink density and poorly oxidation-stabilized material would yield a low PF value, whereas a high crosslink density and highly oxidation resistant materials yield a high PF.

In one embodiment performance factor $PF_{OIT}$ can be used to determine the antioxidant or antioxidant mixture to be used with production UHMWPE materials to provide improve performance with respect to wear resistance and oxidation resistance. $PF_{OIT}$ can be calculated as the product of the crosslink density and OIT.

In another embodiment performance factor $PF_{OI-rate}$ can be used to determine the antioxidant or antioxidant mixture to be used with production UHMWPE materials to provide improve performance with respect to wear resistance and oxidation resistance. $PF_{OI-rate}$ can be calculated as the product of the crosslink density and the inverse of OI-rate.

In one embodiment, a UHMWPE article can have a $PF_{OIT}$ of greater than about 0.06 min*mol/dm^3. In another embodiment, a UHMWPE article can have a $PF_{OIT}$ of greater than about 0.09 min*mol/dm^3. In yet another embodiment a UHMWPE article can have a $PF_{OIT}$ of greater than about 1.2 min*mol/dm^3. In still another embodiment a UHMWPE article can have a $PF_{OIT}$ of greater than about 1.5 min*mol/dm^3. In another embodiment a UHMWPE article can have a $PF_{OIT}$ of greater than about 2.0 min*mol/dm^3. In yet another embodiment a UHMWPE article can have a $PF_{OIT}$ of greater than about 3.0 min*mol/dm^3. In still another embodiment a UHMWPE article can have a $PF_{OIT}$ of greater than about 4.0 min*mol/dm^3.

In one embodiment, a UHMWPE article can have a $PF_{OI\text{-}rate}$ of greater than about 1000 mol/dm^3*wk/OI. In another embodiment, a UHMWPE article can have a $PF_{OI\text{-}rate}$ of greater than about 2500 mol/dm^3*wk/OI. In yet another embodiment a UHMWPE article can have a $PF_{OI\text{-}rate}$ of greater than about 4000 mol/dm^3*wk/OI. In still another embodiment a UHMWPE article can have a $PF_{OI\text{-}rate}$ of greater than about 5000 mol/dm^3*wk/OI. In another embodiment a UHMWPE article can have a $PF_{OI\text{-}rate}$ of greater than about 7500 mol/dm^3*wk/OI. In yet another embodiment a UHMWPE article can have a $PF_{OI\text{-}rate}$ of greater than about 11.500 mol/dm^3*wk/OI.

In another embodiment, a method for selecting one or more antioxidants for providing effective long term oxidation resistance for use in a UHMWPE and antioxidant blend can include measuring the OIT of samples including a blend of UHMWPE and the one or more antioxidants to be selected and selecting the one or more antioxidants included in the sample having a higher OIT. In one embodiment a UHMWPE article can have an OIT of greater than 15 minutes.

In another embodiment, a method for selecting one or more antioxidants for providing effective long term oxidation resistance for use in a UHMWPE and antioxidant blend can include measuring the OI of samples including a blend of UHMWPE and the one or more antioxidants to be selected and selecting the one or more antioxidants included in the sample having a lower OI-rate. In one embodiment a UHMWPE article can have an OI-rate of less than 0.006 OI per week (OI/week).

In general there appears a broad agreement between OI-rate and OIT, but specific antioxidant performance may also be sensitive to the size and structure of individual antioxidant molecule.

Figure 12:
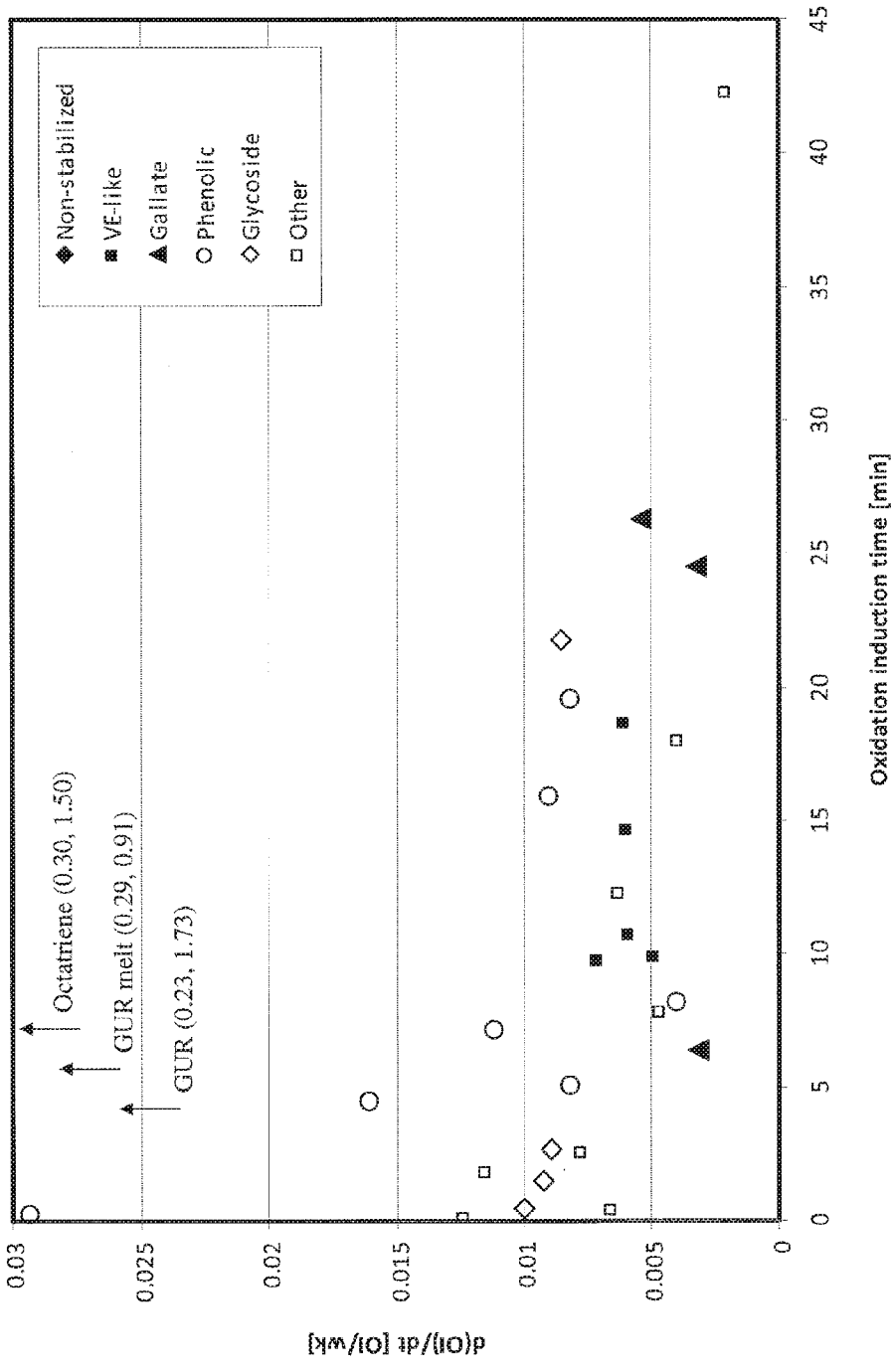
FIG. 12 shows a graph of OI-rate versus OIT of samples including a blend of UHMWPE and a variety of one or more antioxidants.

The chemical structure of the antioxidant such as molecule size, hydroxyl and aryl functional groups, and solubility in non-polar environments may also provide predictive value in terms of providing effective oxidation resistance to UHMWPE and antioxidant blends. As shown in the EXAMPLE section below, samples with antioxidants of similar structure show general groupings with respect to OIT and OI-rate values. (See FIG. 12). For example, VE-like antioxidants are closely grouped in FIG. 12, despite marked differences in both the various chroman "heads" (alpha- versus gamma-tocopherol) and hydrocarbon "tails" (VE versus Trolox versus chromanol). The two "other" formulations similar to the VE-like antioxidants with respect to FIG. 12 are VE/Doverphos blends, and the two "phenolic" formulations nearby are curcumin and resveratrol, both very similar molecules that share some aspects of the VE-like molecules including phenolic heads joined by hydrocarbon bridges (rather than tails). The gallate samples bracket the VE-like samples in terms of OIT, and are even closer in structure to VE, with simpler phenolic heads and hydrocarbon tails of varying length.

The respective lengths of hydrocarbon tails of some antioxidants can be of potential interest as longer hydrocarbon tails may provide increased solubility in non-polar environments such as UHMWPE. While all VE-like antioxidants performed similarly in terms of OI-rate, those with longer hydrocarbon tails showed much longer OIT values, with the exception of the VE/Trolox blend. Gallate formulations ranked in the same manner in terms of OIT, with longer OIT values exhibited by antioxidants with longer hydrocarbon tails, but trended in the opposite direction in terms of OI-rate. The observed OIT measurements (taken when the sample was melted) could yield different rankings than those yielded by OI-rate due to markedly different diffusion rates or solubility in the two conditions, both due to chemical structure and molecule size.

Those samples underperforming VE had either very short hydrocarbon "tails", leading to lowered solubility in hydrophobic environments for Trolox and chromanol, or reduced steric hindrance at the phenolic hydroxyl in the case of g-T. Samples with superior performance to VE include both long-tail gallates, VE/Trolox blend, DP/VE and DP/lauryl gallate. While being held to any theory about why the addition of a hydrocarbon tail to gallic acid improves its performance, but it is possible that hydrophobic regions in the gallates allow micelle formation, and therefore increased solubility in UHMWPE.

Identifying antioxidants in terms of their ability to react with free radicals i.e. whether the antioxidant can be categorized as a primary (1°) antioxidant, which is known or suspected to react directly with free peroxy radicals (ROO*) through the process of donating a hydrogen to the peroxy free radical, or as a secondary (2°) antioxidant which is known to react with hydroperoxides (ROOH) to yield non-reactive species may also be indicative of oxidation resistance. Hindered phenols, tocopherols, and secondary aromatic amines are common primary antioxidants. In addition, the commercially available secondary (2°) antioxidant Doverphos® (DP) was blended with several 1° antioxidant formulations.

As shown in the EXAMPLE section below, the addition of 2° antioxidants to certain 1° antioxidant produces increased performance in both OI-rate and OIT, which may be evidence of comparative effects between these molecules. Further investigation into the structure of the molecules tested and optimal concentration ratios may yield performance still better than the effective AO formulations tested here.

The Examples of 1°/2° AO blends indicate that the amount of 2° AO can affect blend performance. The VE/DP blend with more DP than VE ranked below pure VE, while the 1:1 ratio ranked above pure VE, and the formulation with the least DP ranked further up still. Adding DP on top of the full 0.2 wt % VE improved performance still.

In one embodiment, an article includes a blend of UHMWPE and an antioxidant or antioxidant mixture selected from the group consisting of lauryl gallate, octyl gallate, propyl gallate, curcumin, resveratrol, rutin, Doverphos and vitamin E mixture, Doverphos and lauryl gallate mixture, Trolox and vitamin E mixture, Trolox, gamma tocopherol, and tannic acid.

In another embodiment an article such as an implantable article includes a blend of UHMWPE and an antioxidant or antioxidant mixture selected from the group consisting of lauryl gallate, octyl gallate, propyl gallate, curcumin, resveratrol, rutin, Doverphos and vitamin E mixture, Doverphos and lauryl gallate mixture, Trolox and vitamin E mixture, Trolox, gamma tocopherol, and tannic acid wherein each antioxidant can be included at a concentration of from about 0.01% to about 2% by weight.

In one embodiment, an article can include a blend of UHMWPE and 1° antioxidant and a 2° antioxidant wherein the concentration of the 1° antioxidant is greater than the concentration of the 2° antioxidant.

In another embodiment an article such as implantable article can include a blend of UHMWPE and first and second antioxidants wherein the article has one or more of a crosslink density of greater than 0.075 mol/dm³, an oxidation induction time of greater than 15 minutes and an oxidation index-rate of greater than 0.006 OI/week.

In another embodiment an article such as an implantable article can include a blend of UHMWPE and lauryl gallate at a concentration of from about 0.05 to about 1% by weight.

In yet another embodiment an article such as an implantable article can include a blend of UHMWPE and octyl gallate at a concentration of from about 0.05 to about 1% by weight.

In still another embodiment an article such as an implantable article can include a blend of UHMWPE and propyl gallate at a concentration of from about 0.05 to about 1% by weight.

In another embodiment an article such as an implantable article can include a blend of UHMWPE and curcumin at a concentration of from about 0.05 to about 1% by weight.

In yet another embodiment an article such as an implantable article can include a blend of UHMWPE and resveratrol at a concentration of from about 0.05 to about 1% by weight.

In yet another embodiment an article such as an implantable article can include a blend of UHMWPE and rutin at a concentration of from about 0.05 to about 1% by weight.

In still another embodiment an article such as an implantable article can include a blend of UHMWPE and Irganox at a concentration of from about 0.05 to about 1% by weight.

In another embodiment an article such as an implantable article can include a blend of UHMWPE and Trolox at a concentration of from about 0.05 to about 1% by weight.

In yet another embodiment an article such as an implantable article can include a blend of UHMWPE and tannic acid at a concentration of from about 0.05 to about 1% by weight.

In still another embodiment an article such as an implantable article can include a blend of UHMWPE and gamma tocopherol at a concentration of from about 0.05 to about 1% by weight.

In another embodiment an article such as an implantable article can include a blend of UHMWPE and Doverphos at a concentration of from about 0.05 to about 1% by weight and vitamin E mixture at a concentration of from about 0.05 to about 1% by weight.

In yet another embodiment an article such as an implantable article can include a blend of UHMWPE and Doverphos at a concentration of from about 0.05 to about 1% by weight and lauryl gallate at a concentration of from about 0.05 to about 1% by weight.

In still another embodiment an article such as an implantable article can include a blend of UHMWPE and Trolox at a concentration of from about 0.05 to about 1% by weight and vitamin E mixture at a concentration of from about 0.05 to about 1% by weight.

In another embodiment an article such as an implantable article can include a blend of UHMWPE and lauryl gallate at a concentration of about 0.2% by weight.

In yet another embodiment an article such as an implantable article can include a blend of UHMWPE and octyl gallate at a concentration of about 0.2% by weight.

In still another embodiment an article such as an implantable article can include a blend of UHMWPE and propyl gallate at a concentration of about 0.2% by weight.

In another embodiment an article such as an implantable article can include a blend of UHMWPE and curcumin at a concentration of about 0.2% by weight.

In yet another embodiment an article such as an implantable article can include a blend of UHMWPE and resveratrol at a concentration of about 0.2% by weight.

In yet another embodiment an article such as an implantable article can include a blend of UHMWPE and rutin at a concentration of about 0.2% by weight.

In still another embodiment an article such as an implantable article can include a blend of UHMWPE and Irganox at a concentration of about 0.2% by weight.

In another embodiment an article such as an implantable article can include a blend of UHMWPE and Trolox at a concentration of about 0.2% by weight.

In yet another embodiment an article such as an implantable article can include a blend of UHMWPE and tannic acid at a concentration of about 0.2% by weight.

In still another embodiment an article such as an implantable article can include a blend of UHMWPE and gamma tocopherol at a concentration of about 0.2% by weight.

In another embodiment an article such as an implantable article can include a blend of UHMWPE and Doverphos at a concentration of about 0.05% by weight and vitamin E at a concentration of about 0.15% by weight.

In yet another embodiment an article such as an implantable article can include a blend of UHMWPE and Doverphos at a concentration of about 0.1% by weight and lauryl gallate at a concentration of about 0.1% by weight.

In still another embodiment an article such as an implantable article can include a blend of UHMWPE and Trolox at a concentration of about 0.1% by weight and vitamin E mixture at a concentration of about 0.1% by weight.

EXAMPLES

Sample formulations were prepared by blending GUR 1050 UHMWPE powder from Ticona with one or more antioxidants shown in Table 2 below. The one or more antioxidants were dissolved in a solvent such as isopropyl alcohol or ethanol, if in liquid form, whereas solid forms were just added directly and mixed with the GUR 1050 powder. The solvent was removed using a fluidized bed dryer and then consolidated into pucks in a nitrogen atmosphere using compression molding. The pucks were irradiated using electron-beam radiation to 100 kGy by Sterigenics. Two control formulations were prepared in the same manner but without any antioxidant included. One of the control samples (GUR melt) received an annealing or melt process and the other control (GUR) and antioxidant containing samples did not undergo annealing or melt process.

The antioxidant was added to provide an active ingredient of 0.2% by weight of the total mass of the sample unless indicated otherwise in the Table 2 below. For example, the samples containing bilberry which was supplied as an extract having a 25% bilberry concentration was tested at 0.2 wt % and 0.8 wt % of the extract, providing effectively 0.05 wt % and 0.2 wt % active ingredient. For the samples containing more than one antioxidant such as the sample containing both Trolox and vitamin E, Trolox was included at a concentration of 0.1% by weight and vitamin E was included at a concentration of 0.1% by weight unless otherwise indicated in Table 2 below. Samples were stored under vacuum in light-opaque packaging in 0° C. freezers when not in use.

TABLE 2

| Antioxidant | Concentration (by percent weight) |
|---|---|
| Vitamin E, (VE) (□-tocopherol) | 0.20% |
| Gamma-tocopherol (g-T) (γ-tocopherol) | 0.20% |

TABLE 2-continued

| Antioxidant | Concentration (by percent weight) |
|---|---|
| Trolox | 0.20% |
| Trolox/VE | (0.1%/0.1%) |
| 2,2,5,7,8-penta-methyl-6-chromanol (Chromanol) | 0.20% |
| Lauryl Gallate (L. gallate) | 0.20% |
| Octyl Gallate (O. gallate) | 0.20% |
| Propyl Gallate (P. gallate) | 0.20% |
| Curcumin | 0.20% |
| Resveratrol | 0.20% |
| Catechin | 0.20% |
| Chlorogenic acid | 0.20% |
| Tannic acid | 0.20% |
| Gallic acid | 0.20% |
| Ellagic acid | 0.20% |
| Bilberry | 0.20% |
| Bilberry | 0.05% |
| Rutin | 0.20% |
| Hesperidin | 0.20% |
| Naringin | 0.20% |
| Doverphos (DP) | 0.20% |
| DP/VE | (0.05/0.15) |
| DP/VE | (0.1/0.1) |
| DP/VE | (0.15/0.05) |
| DP/VE | (0.2/0.2) |
| DP/L. gal | (0.1/0.1) |
| a-lipoic acid | 0.20% |
| Genox | 0.20% |
| Vitamin C (VC) | 0.20% |
| 2,6-dimethyl-2,4,6-octratriene (Octatriene) | 0.20% |
| Irganox 1010 | 0.20% |

The samples were tested to determine mechanical properties, crosslink density, OIT and OI. The mechanical properties, crosslink density and OIT were tested prior to any simulated aging. Samples were tested for OI at an initial or zero time and then subjected to simulated or accelerated aging and tested periodically as discussed below in greater detail to establish an OI-rate for each of the samples.

The sample pucks were tested for mechanical properties with the results shown in Table 3 below. Testing samples were taken from the pucks for each of the mechanical property tests according to ASTM D638 and D256 methods.

TABLE 3

| | Average value | | | | Standard deviation | | | |
|---|---|---|---|---|---|---|---|---|
| Sample | UTS MPa | Strain @ break % | Yield stress MPa | IZOD kJ/m$^2$ | UTS MPa | Strain @ break % | Yield stress MPa | IZOD kJ/m$^2$ |
| GUR 1050 | 66.8 | 398.8 | 21.9 | 1122.8 | 6.5 | 24.4 | 0.4 | 2.4 |
| GUR 1050 melt | 59.4 | 300.6 | 23.3 | 75.7 | 4.2 | 14.1 | 0.5 | 1.2 |
| VE | 63.2 | 355.4 | 23.4 | 92.9 | 5.1 | 16.5 | 0.3 | 3.0 |
| g-T | 63.1 | 351.6 | 22.8 | 82.4 | 5.4 | 15.6 | 0.4 | 2.1 |
| Trolox | 56.2 | 346.5 | 23.1 | 97.3 | 3.9 | 14.9 | 0.3 | 2.8 |
| Trolox/VE (0.1/0.1) | 54.3 | 345.0 | 23.2 | 98.5 | 6.4 | 26.4 | 0.5 | 2.0 |
| Chromanol | 63.7 | 390.2 | 23.5 | 107.9 | 6.7 | 21.9 | 0.2 | 2.2 |
| L. gallate | 61.7 | 356.4 | 23.5 | 99.5 | 7.2 | 27.6 | 0.5 | 3.4 |
| O. gallate | 60.8 | 366.1 | 23.0 | 91.4 | 6.7 | 22.9 | 0.2 | 2.7 |
| P. gallate | 62.9 | 329.6 | 22.7 | 75.6 | 2.2 | 7.6 | 0.2 | 1.5 |
| Curcumin | 54.5 | 287.1 | 23.1 | 79.0 | 4.8 | 20.3 | 0.3 | 1.8 |
| Resveratrol | 42.7 | 243.7 | 23.4 | 77.2 | 2.1 | 11.2 | 0.2 | 1.3 |
| Catechin | 52.4 | 275.4 | 23.5 | 71.7 | 3.4 | 10.2 | 0.3 | 1.8 |
| Chlorogenic acid | 44.9 | 247.5 | 23.6 | 75.3 | 5.2 | 23.8 | 0.3 | 1.0 |
| Tannic acid | 52.4 | 276.5 | 22.7 | 69.9 | 2.7 | 9.3 | 0.1 | 2.6 |
| Gallic acid | 42.8 | 243.0 | 22.5 | 63.4 | 2.2 | 9.1 | 0.4 | 1.6 |
| Ellagic acid | 42.6 | 246.5 | 22.7 | 67.3 | 3.1 | 12.0 | 0.3 | 2.2 |
| Bilberry (0.2) | 44.2 | 244.2 | 23.3 | 75.8 | 2.8 | 12.0 | 0.3 | 2.0 |
| Bilberry (0.8) | 37.3 | 214.7 | 23.3 | 77.2 | 1.5 | 8.5 | 0.3 | 2.3 |
| Rutin | 52.5 | 281.7 | 23.3 | 74.3 | 5.9 | 19.6 | 0.3 | 2.0 |
| Hesperidin | 50.0 | 271.8 | 22.8 | 69.1 | 1.9 | 8.4 | 0.2 | 1.4 |
| Naringin | 51.3 | 273.1 | 22.5 | 69.3 | 2.9 | 11.6 | 0.5 | 2.1 |
| Doverphos (DP) | 58.7 | 304.2 | 23.4 | 76.1 | 4.8 | 19.3 | 0.3 | 1.5 |
| DP/VE (0.05/0.15) | 58.9 | 342.7 | 22.5 | 82.6 | 6.3 | 23.8 | 0.2 | 1.5 |
| DP/VE (0.10/0.10) | 55.4 | 307.9 | 23.4 | 86.7 | 5.2 | 20.4 | 0.6 | 1.8 |
| DP/VE (0.15/0.05) | 57.9 | 314.2 | 23.1 | 75.3 | 6.5 | 23.6 | 1.3 | 1.9 |
| DP/VE (0.20/0.20) | 57.4 | 346.3 | 22.6 | 87.3 | 8.0 | 38.8 | 0.4 | 1.6 |
| DP/L. gal (0.1/0.1) | 58.8 | 337.3 | 22.7 | 86.2 | 5.8 | 23.1 | 0.3 | 3.7 |
| a-lipoic acid | 60.8 | 351.7 | 23.3 | 96.8 | 8.5 | 28.3 | 0.4 | 2.7 |
| Genox | 55.4 | 284.5 | 23.2 | 74.2 | 6.7 | 22.9 | 0.7 | 1.8 |
| VC | 52.2 | 281.3 | 22.8 | 66.8 | 2.7 | 11.3 | 0.4 | 1.1 |
| Octatriene | 59.5 | 292.4 | 23.5 | 75.2 | 6.4 | 16.7 | 0.3 | 1.6 |
| Irg (0.075) | 66.4 | 352.3 | 23.9 | 75.2 | 4.6 | 17.3 | 0.3 | 3.1 |
| Irg (0.2) | 62.2 | 325.2 | 22.7 | 76.2 | 3.2 | 9.5 | 0.5 | 1.8 |

The samples were tested for crosslink density using swell ratio in accordance with ASTM F 2214-02. Five millimeter cube specimens are machined from the sample pucks and tested at 130° C. in o-xylene (97% Sigma) with 1 wt % Irganox 1010 (Ciba) and results are reported in mol/dm^3. Results are shown below in Table 4 with most samples graphically represented in FIG. 1.

TABLE 4

| | Crosslink Density | |
|---|---|---|
| Sample | Average value mol/dm$^3$ | Standard deviation mol/dm$^3$ |
| GUR melt | 0.194 | 0.012 |
| GUR | 0.154 | 0.017 |
| VE | 0.074 | 0.003 |
| g-T | 0.111 | 0.006 |
| Trolox | 0.113 | 0.011 |
| Trolox/VE (0.1/0.1) | 0.101 | 0.012 |
| Chromanol | 0.077 | 0.010 |
| L. gallate | 0.089 | 0.007 |
| O. gallate | 0.091 | 0.007 |
| P. Gallate | 0.140 | 0.022 |
| Curcumin | 0.158 | 0.021 |
| Resveratrol | 0.128 | 0.012 |
| Catechin | 0.119 | 0.020 |
| Chlorogenic acid | 0.121 | 0.002 |
| Tannic acid | 0.145 | 0.016 |
| Gallic acid | 0.145 | 0.023 |
| Ellagic acid | 0.192 | 0.042 |
| Bilberry (0.2) | 0.197 | 0.007 |
| Bilberry (0.8) | 0.175 | 0.021 |
| Rutin | 0.127 | 0.011 |
| Hesperidin | 0.115 | 0.030 |
| Naringin | 0.173 | 0.031 |
| Doverphos (DP) | 0.137 | 0.015 |
| DP/VE (0.05/0.15) | 0.107 | 0.038 |
| DP/VE (0.10/0.10) | 0.145 | 0.021 |
| DP/VE (0.15/0.05) | 0.099 | 0.026 |
| DP/VE (0.20/0.20) | 0.109 | 0.013 |
| DP/L. gal (0.1/0.1) | 0.098 | 0.031 |
| a-lipoic acid | 0.079 | 0.016 |
| Genox | 0.156 | 0.019 | 0.019 |
| VC | 0.128 | 0.014 |
| Octatriene | 0.143 | 0.035 |
| Irg (0.075) | 0.110 | 0.013 |
| Irg (0.2) | 0.119 | 0.011 |

The samples were also tested for OFT by differential scanning calorimetry using a DSC, Q1000 from Thermal Advantage Instruments, Newcastle, Del. in accordance with ASTM D 3895-98 (offset method) and ASTM 3895-07 (tangent method). Oxidation Induction Time is a measurement of the time interval to onset of exothermic degradation at a specified temperature in an oxygen atmosphere. Test specimens of about 200 µm thick and 6 mm in diameter were taken from the sample pucks. Films were prepared by cross-sectioning the sample pucks with a bandsaw and then slicing with a microtome to produce a thin film (approximately 200 µm) perpendicular to the top and bottom surfaces of the puck. Specimens were prepared by punching a disc from the film with a 6 mm punch.

Figure 2:
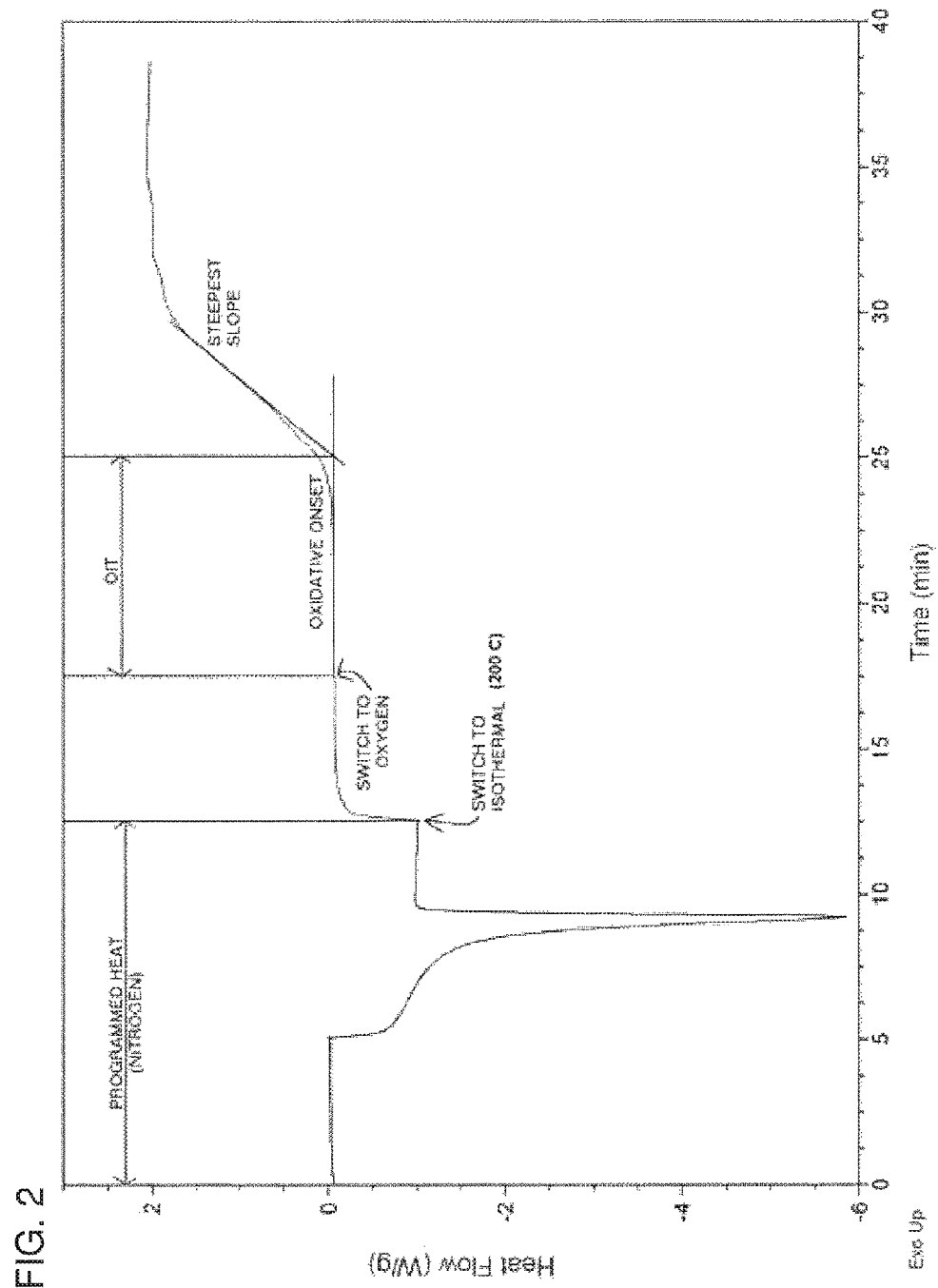
FIG. 2 shows heat flow diagram of an OIT testing protocol.

The specimen was weighed on a precision balance (AND GR-202, 0.01 mg). The balance is routinely calibrated with precision masses. The specimen was placed in an open aluminum pan and placed in the cell. An empty aluminum pan was used as a reference. Prior to testing, the DSC was calibrated with indium standards according to CPG Standard Operating Procedures. A 50 ml/min nitrogen purge was used. After equilibration at ambient temperature, the cell was heated at 20° C./min to 200° C. After remaining isothermal at this temperature for 5 minutes, the purge was switched to a 50 ml/min oxygen flow. Using this changeover as time zero, the time required for an exotherm due to degeneration to build was monitored. Data collection was stopped after the full completion of the exotherm and the stabilization of the heat flow within the DSC. From the data, TA Advantage Universal Analysis software was used to determine the OIT using the maximum slope tangent to baseline intercept method as depicted in FIG. 2.

Figure 3:
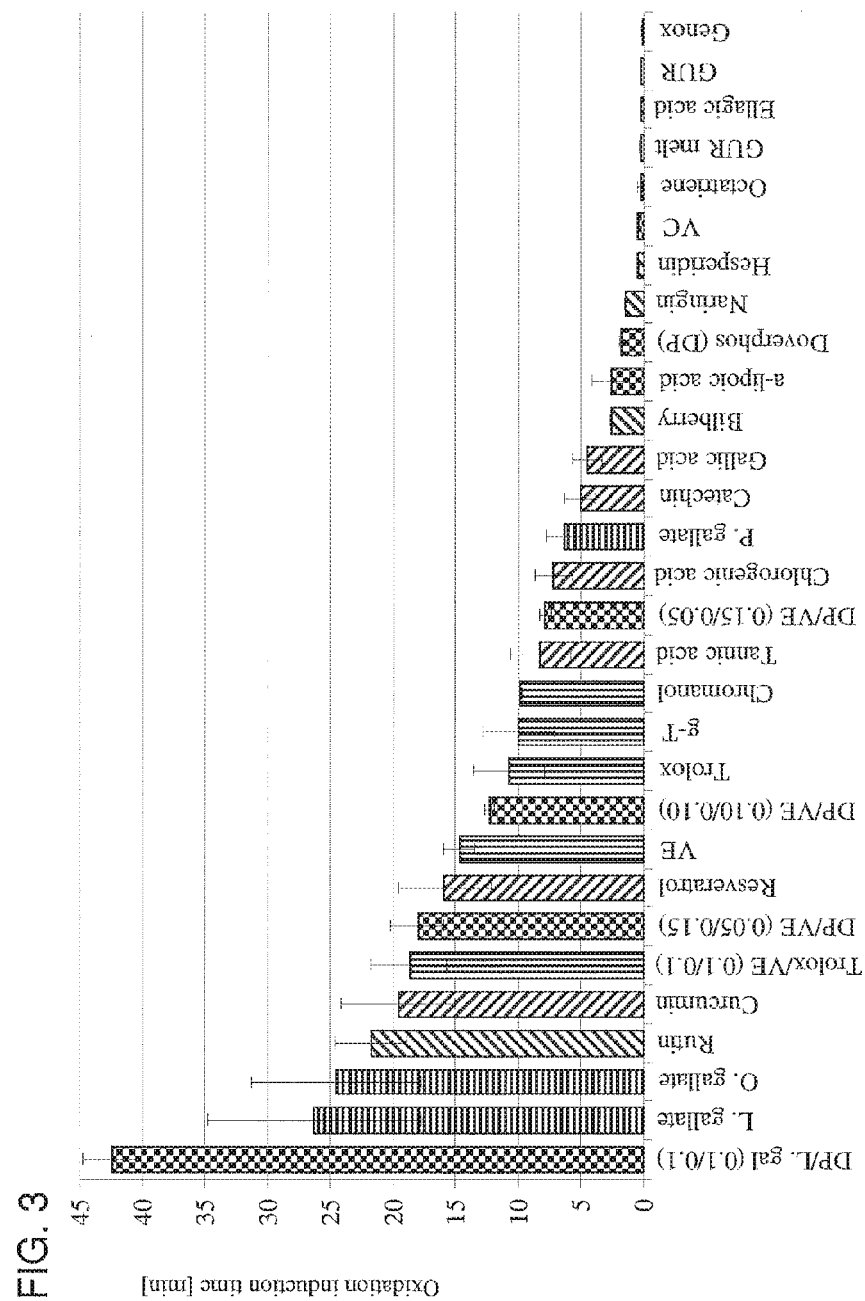
FIG. 3 shows a graph of crosslink density values of samples including a blend of UHMWPE and a variety of one or more antioxidants.

The results of the OIT testing are shown in Table 5 below for both the offset and tangent method. The OIT offset method results are shown graphically in FIG. 3 and Off offset method values were used in all the following comparisons such as OIT versus OI rate in FIG. 12 and the following calculations such as PF$_{OIT}$ and PF$_{OI\text{-}rate}$.

TABLE 5

| | Oxidation Induction Time (OIT) | | | |
|---|---|---|---|---|
| | Average value | | Standard deviation | |
| Sample | Tangent method minutes | Offset method minutes | Tangent method minutes | Offset method minutes |
| GUR melt | 2.4 | 0.3 | 1.9 | 0.0 |
| GUR | 0.7 | 0.2 | 0.3 | 0.0 |
| VE | 17.7 | 14.7 | 2.0 | 1.3 |
| g-T | 14.3 | 10.0 | 1.6 | 2.8 |
| Trolox | 15.0 | 10.8 | 2.9 | 2.9 |
| Trolox/VE (0.1/0.1) | 22.4 | 18.7 | 2.9 | 3.0 |
| Chromanol | 12.1 | 9.8 | 0.7 | 0.1 |
| L. gallate | 32.3 | 26.3 | 6.0 | 8.5 |
| O. gallate | 31.8 | 24.5 | 2.8 | 6.7 |
| P. Gallate | 12.2 | 6.4 | 1.6 | 1.4 |
| Curcumin | 22.0 | 19.6 | 3.8 | 4.6 |
| Resveratrol | 20.6 | 15.9 | 1.0 | 3.7 |
| Catechin | 7.6 | 5.1 | 1.1 | 1.2 |
| Chlorogenic acid | 10.2 | 7.2 | 2.5 | 1.5 |
| Tannic acid | 11.3 | 8.3 | 2.2 | 2.4 |
| Gallic acid | 6.5 | 4.6 | 1.5 | 1.1 |
| Ellagic acid | 2.6 | 0.3 | 1.3 | 0.0 |
| Bilberry (0.2) | 2.5 | 1.0 | 0.8 | 0.0 |
| Bilberry (0.8) | 4.8 | 2.7 | 0.1 | 0.1 |
| Rutin | 35.4 | 21.7 | 1.1 | 2.8 |
| Hesperidin | 2.0 | 0.5 | 0.7 | 0.1 |
| Naringin | 3.2 | 1.5 | 0.3 | 0.1 |
| Doverphos (DP) | 4.4 | 1.9 | 1.1 | 0.1 |
| DP/VE (0.05/0.15) | 20.6 | 18.1 | 0.7 | 2.2 |
| DP/VE (0.10/0.10) | 15.4 | 12.3 | 1.1 | 0.4 |
| DP/VE (0.15/0.05) | 8.8 | 7.9 | 1.0 | 0.5 |
| DP/VE (0.20/0.20) | 29.5 | 27.0 | 1.0 | 1.2 |
| DP/L. gal (0.1/0.1) | 46.4 | 42.4 | 0.9 | 2.4 |
| a-lipoic acid | 5.2 | 2.6 | 0.3 | 1.5 |
| Genox | 3.2 | 0.2 | 1.2 | 0.1 |
| VC | 2.1 | 0.5 | 1.2 | 0.0 |
| Octatriene | 2.0 | 0.3 | 1.1 | 0.2 |
| Irg (0.075) | 8.0 | 6.3 | 0.7 | 1.1 |
| Irg (0.2) | 36.5 | 29.1 | 3.3 | 6.6 |

OIT showed a wide range of responses, with some samples including an antioxidant oxidizing so quickly that they are indistinguishable from the GUR 1050 controls. See FIG. 3. Calculation of very short OIT values (<1 minute) may not be as accurate as longer OIT values due to the very small amount of pre-reaction data available in the raw heat trace for construction of the baseline and the rapid onset of oxidation in some of the samples.

The samples were also tested for Oxidation Index (OI). OI was measured by transmission Fourier-transform infrared spectroscopy (FT-IR, FTS3000 bench with UMA500 microscope, Bio-Rad) in accordance with ASTM F 2102-01 prior to accelerated or simulated aging process and then at weekly time points during exposure to accelerated or simulated aging process. The collection parameters are listed as follows:

process. In this simulated or accelerated aging method, FT-IR specimen films were aged in an accelerating aging environment consisting of a digital convection oven (DKN400, Yamato) maintained at 80±2° C. in air. The accelerated aging factor (AAF) was estimated to be 55.7 from the relationship in ASTM F 1980-99e1 (equation 1), standard values for Q10=2 and TRT=22° C., indicating the equivalent of roughly one year of real-time aging for each week of accelerated aging.

The results of OI testing are shown in the Table 6 below.

TABLE 6

| | Oxidation Index | | | | | | | |
|---|---|---|---|---|---|---|---|---|
| Sample | Wk 0 | Wk 1 | Wk 2 | Wk 5 | Wk 7 | Wk 10 | Wk 15 | Wk 20 |
| GUR melt | −0.043 | −0.016 | 0.496 | 1.626 | 4.576 | 9.234 | 9.510 | 9.958 |
| GUR | 0.011 | 0.153 | 1.627 | 6.296 | 12.170 | 12.776 | 12.661 | 2.738 |
| VE | −0.050 | −0.037 | −0.022 | −0.011 | 0.005 | 0.010 | 0.053 | 0.073 |
| g-T | −0.067 | −0.037 | −0.025 | 0.001 | 0.008 | 0.027 | 0.034 | 0.041 |
| Trolox | −0.046 | −0.038 | −0.054 | −0.054 | −0.030 | −0.010 | 0.037 | 0.064 |
| Trolox/VE (0.1/0.1) | −0.055 | −0.044 | −0.012 | −0.006 | −0.003 | 0.001 | 0.055 | 0.074 |
| Chromanol | −0.082 | −0.058 | −0.029 | −0.018 | −0.013 | 0.011 | 0.048 | 0.072 |
| L. gallate | 0.026 | 0.033 | 0.041 | 0.046 | 0.066 | 0.069 | 0.105* | 0.136 |
| O. gallate | 0.032 | 0.056 | 0.072 | 0.073 | 0.096 | 0.099 | 0.103* | 0.106 |
| P. gallate | 0.087 | −0.025 | −0.005 | 0.012 | 0.015 | 0.025 | 0.034* | 0.043 |
| Curcumin | −0.087 | −0.065 | −0.072 | −0.063 | −0.039 | −0.023 | 0.030 | 0.084 |
| Resveratrol | −0.053 | −0.044 | −0.008 | −0.007 | 0.029 | 0.058 | 0.092 | 0.126 |
| Catechin | −0.162 | −0.140 | −0.068 | −0.059 | −0.036 | −0.033 | 0.009 | 0.014 |
| Chlorogenic acid | 0.134 | 0.182 | 0.382 | 0.165 | 0.223 | 0.414 | 0.347 | 0.394 |
| Tannic acid | 0.040 | 0.222 | 0.107 | 0.234 | 0.173 | 0.143 | 0.181* | 0.218 |
| Gallic acid | −0.364 | −0.265 | −0.172 | −0.148 | −0.027 | −0.013 | −0.010* | −0.008 |
| Ellagic acid | 0.358 | 0.538 | 0.614 | 0.655 | 0.570 | 0.867 | 0.932* | 0.997 |
| Bilberry | −0.091 | −0.038 | 0.000 | −0.009 | −0.005 | 0.087 | 0.061 | 0.116 |
| Rutin | −0.130 | −0.097 | −0.053 | −0.030 | −0.024 | 0.021 | 0.039 | 0.051 |
| Hesperidin | −0.117 | −0.054 | −0.031 | 0.026 | 0.044 | 0.031 | 0.076* | 0.122 |
| Naringin | −0.278 | −0.279 | −0.167 | −0.185 | −0.157 | −0.167 | −0.119* | −0.070 |
| Doverphos (DP) | −0.041 | −0.030 | 0.000 | 0.015 | 0.049 | 0.085 | 0.139 | 0.186 |
| DP/VE (0.05/0.15) | −0.076 | −0.052 | −0.022 | −0.007 | 0.004 | 0.010 | 0.013* | 0.017 |
| DP/VE (0.10/0.10) | −0.058 | −0.042 | −0.029 | −0.015 | −0.012 | 0.002 | 0.044 | 0.078 |
| DP/VE (0.15/0.05) | −0.072 | −0.025 | −0.007 | −0.017 | 0.012 | 0.066 | 0.046* | 0.026 |
| DP/VE (0.20/0.20) | −0.093 | −0.066 | −0.026 | −0.019 | −0.009 | −0.003 | 0.003 | 0.002 |
| DP/L. gal (0.1/0.1) | 0.006 | 0.021 | 0.044 | 0.061 | 0.077 | 0.016 | 0.046* | 0.076 |
| a-lipoic acid | 0.165 | 0.143 | 0.160 | 0.179 | 0.192 | 0.228 | 0.284 | 0.288 |
| Genox | −0.031 | 0.019 | 0.017 | 0.028 | 0.066 | 0.110 | 0 189 | 0.219 |
| VC | 0.225 | 0.190 | 0.222 | 0.242 | 0.280 | 0.308 | 0.317* | 0.326 |
| Octatriene | −0.018 | 0.237 | 1.684 | 5.403 | 10.625 | 12.856 | 12.591* | 12.807 |
| Irganox (0.2) | 0.047 | 0.077 | 0.103 | 0.112 | 0.127 | 0.129 | 0.122* | 0.115 |

*signifies the value was generated by averaging the values of previous and following week and shading values indicate an estimated value Aperture size: 200 μm
Apodization: Happ-Genzel
Calibration: Polystyrene
Number of scans: 32
Purge: Nitrogen
Scan rate: 20 kHz
Sensitivity: 4 cm$^{-1}$ Specimens were taken from the sample pucks. Specimen films about 200 μm thick were prepared by cross-sectioning each puck with a bandsaw and then slicing with a microtome to produce a thin film perpendicular to the top and bottom surfaces of the puck. Spectra were obtained from five spots per specimen with an aperture of 200 μm×200 μm, and the resulting OI values were averaged for analysis. OI was calculated as the ratio of area of the carbonyl oxidation peak between 1650-1850 cm$^{-1}$ to the area of the normalization peak between 1363-1396 cm$^{-1}$.

Figure 4:
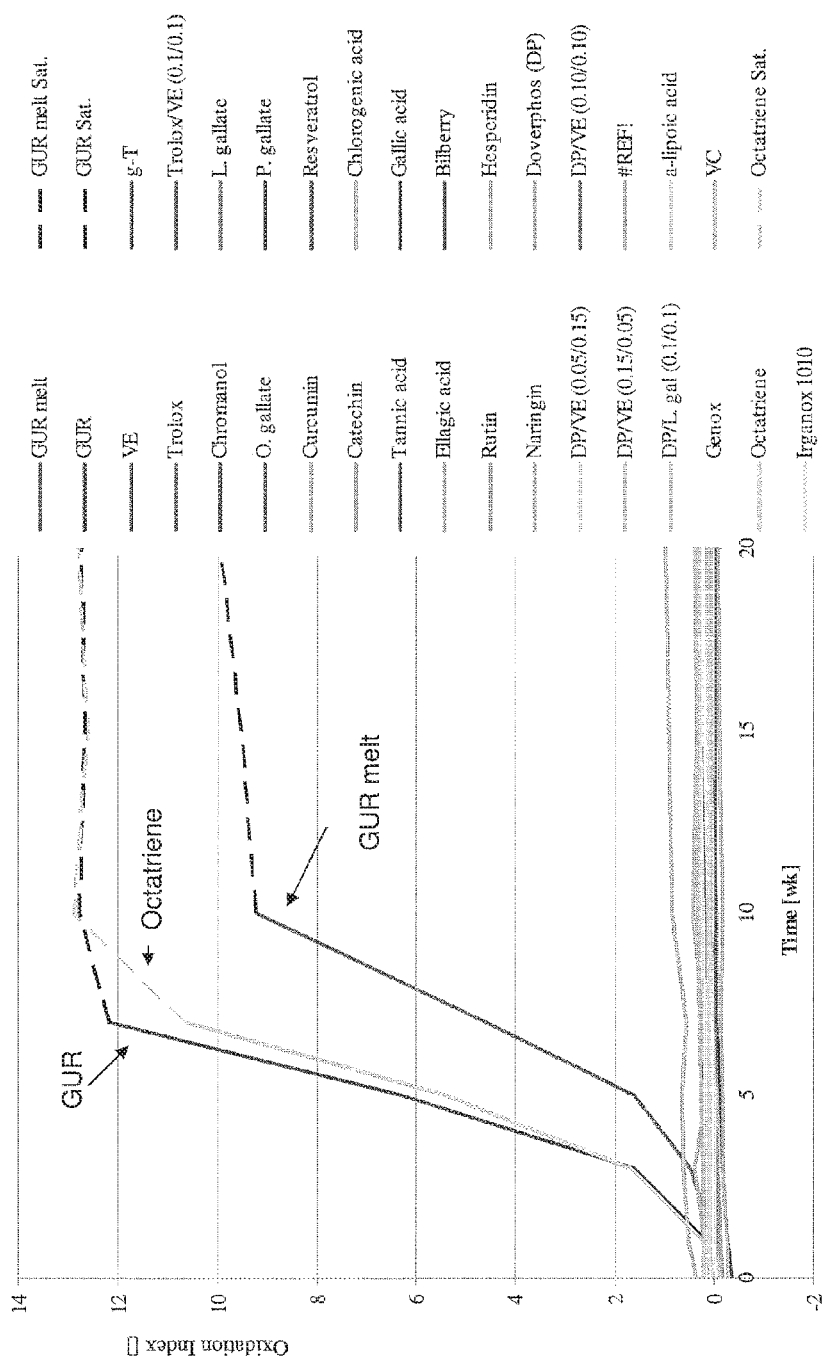
FIG. 4 shows a graph of OI values over time of samples including a blend of UHMWPE and a variety of one or more antioxidants.

The samples were tested for OI at time zero and then the samples were subjected to a simulated or accelerated aging The data in Table 6 is graphically represented in FIGS. 4-10. FIG. 4 shows all the samples. FIG. 4 also shows that OI data for the GUR, GUR melt and octatriene samples have a dashed portion indicating a plateau due to signal saturation.

Figure 5:
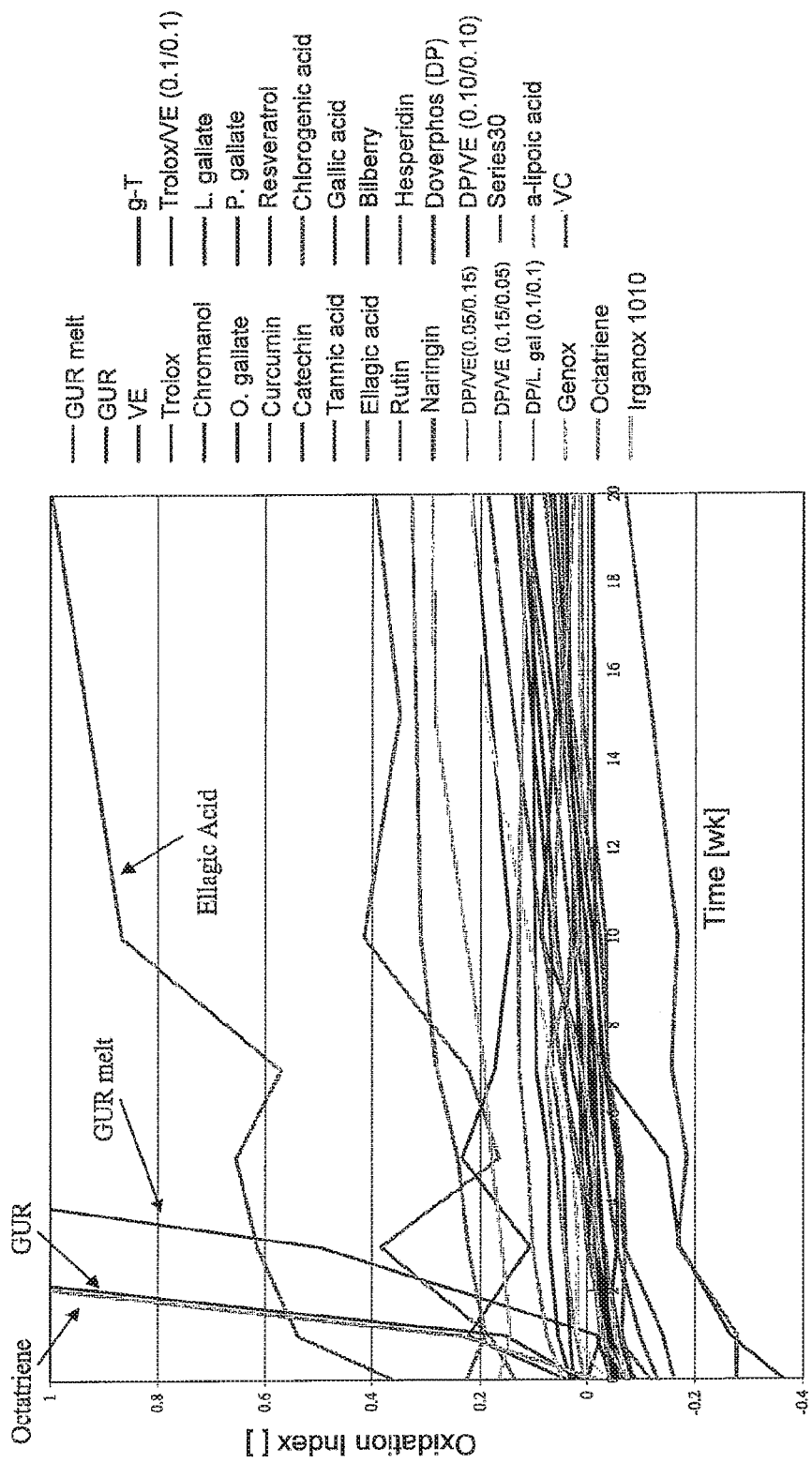
FIG. 5 shows a magnification of the lower portion of the graph of FIG. 4.

FIG. 5 is a magnification of the lower range of OI data shown in FIG. 4.

Figure 6:
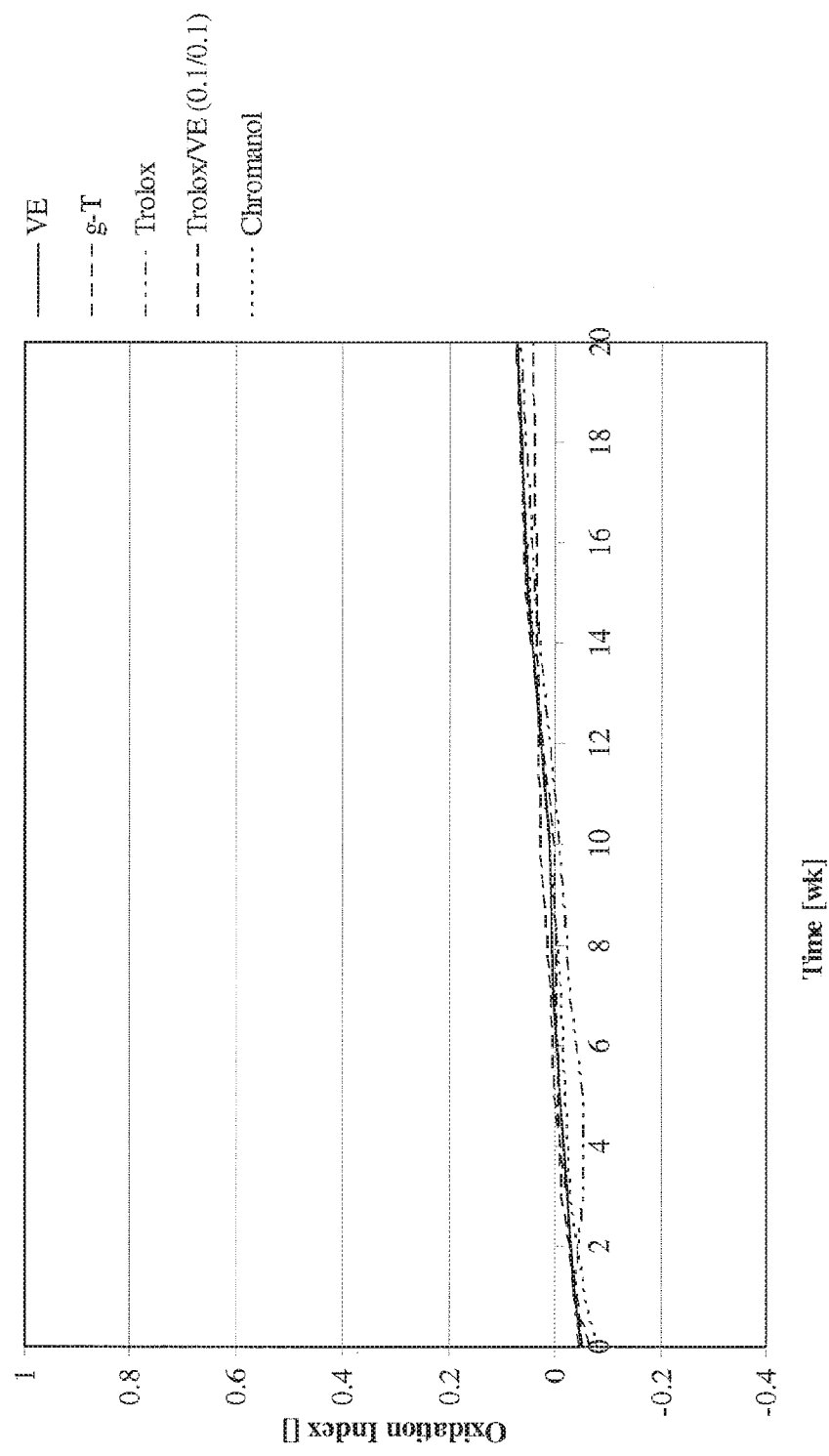
FIG. 6 shows a magnification of the lower portion of the graph of FIG. 4 for samples including VE-like antioxidants.

FIG. 6 shows OI values of samples including VE-like antioxidants.

Figure 7:
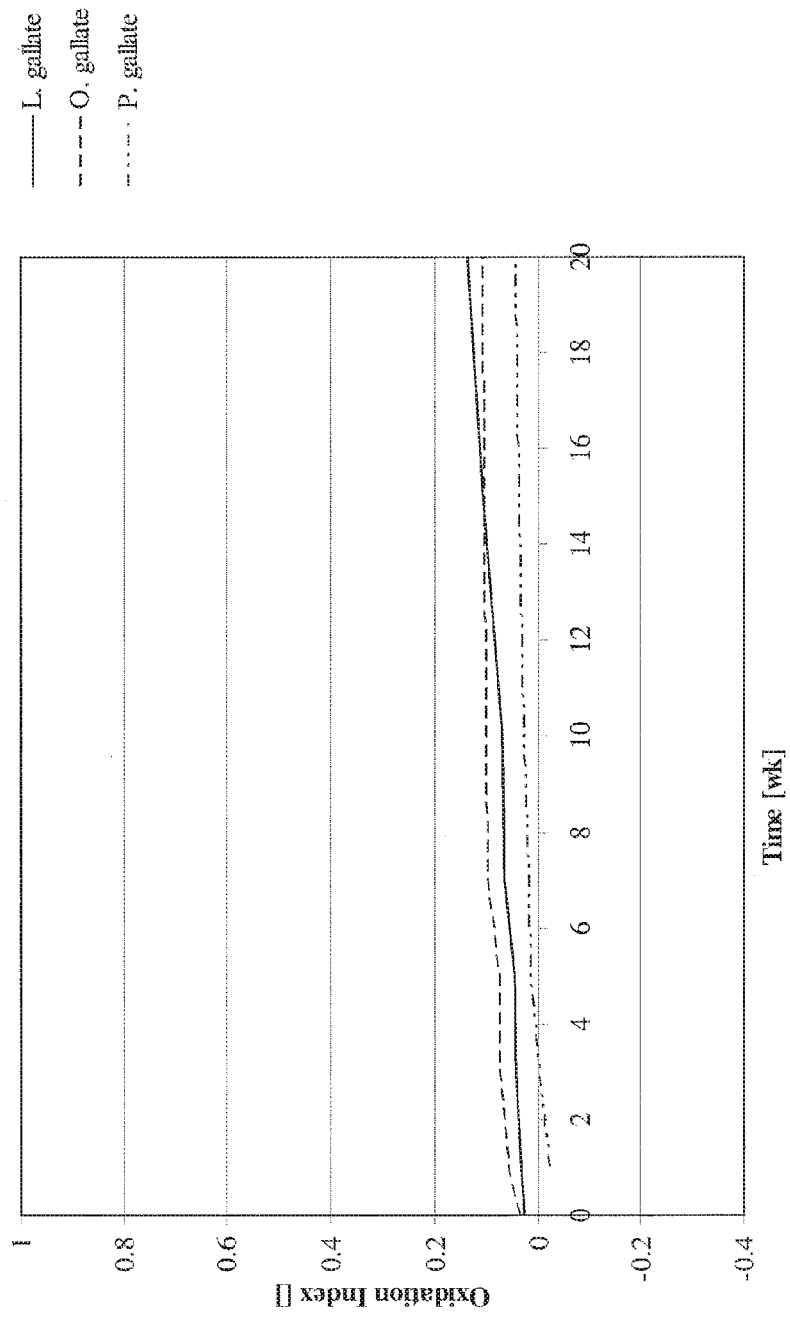
FIG. 7 shows a magnification of the lower portion of the graph of FIG. 4 for samples including gallate-derived antioxidants.

FIG. 7 shows OI values of samples including gallate-derived antioxidants.

Figure 8:
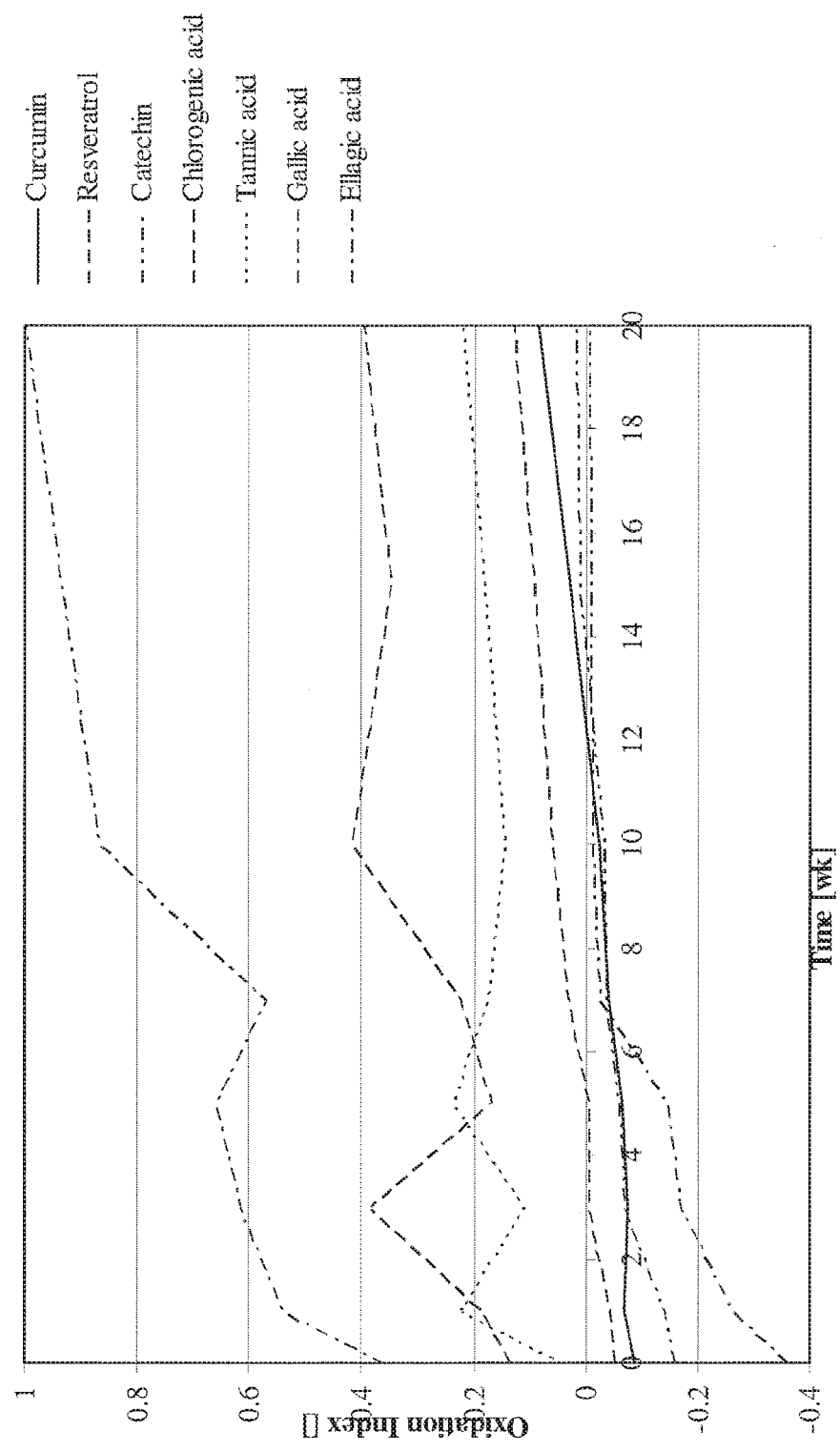
FIG. 8 shows a magnification of the lower portion of the graph of FIG. 4 for samples including phenolic antioxidants.

FIG. 8 shows OI values of samples including phenolic antioxidants.

Figure 9:
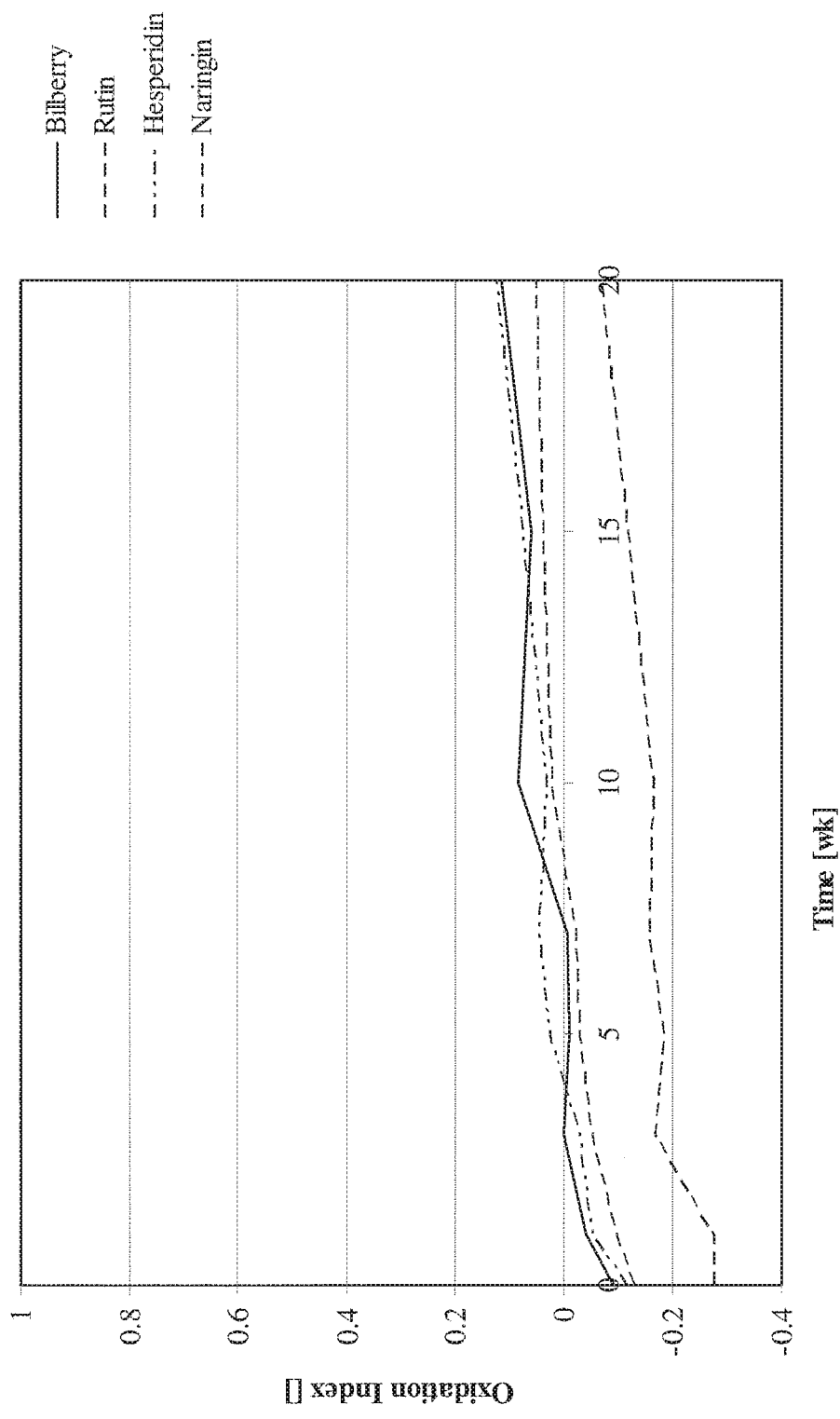
FIG. 9 shows a magnification of the lower portion of the graph of FIG. 4 for samples including glycoside antioxidants.

FIG. 9 shows OI values of samples including glycoside antioxidants.

Figure 10:
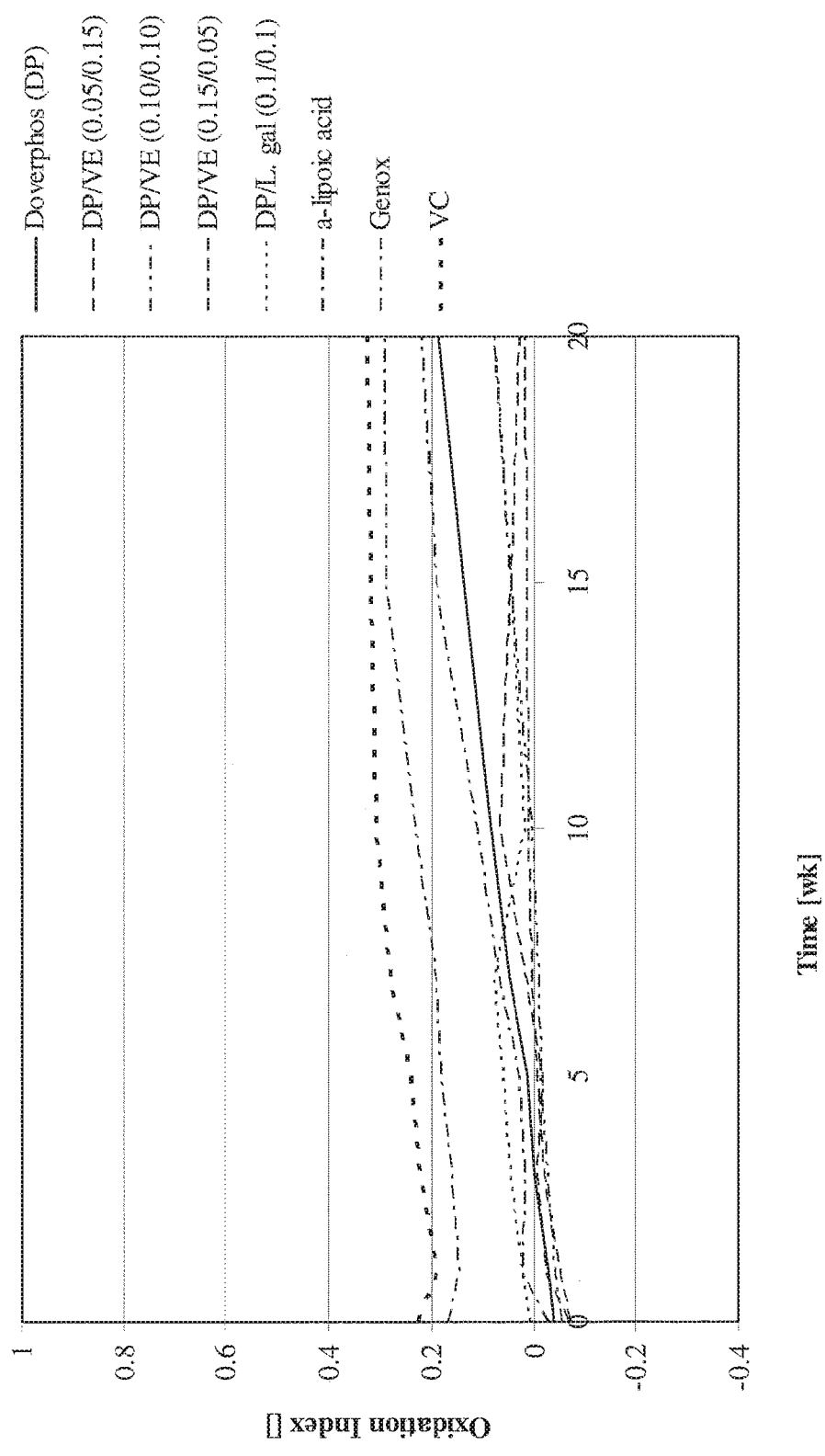
FIG. 10 shows a magnification of the lower portion of the graph of FIG. 4 for samples including other or uncategorized antioxidants.

FIG. 10 shows OI values of samples including other or uncategorized antioxidants.

Figure 10A:
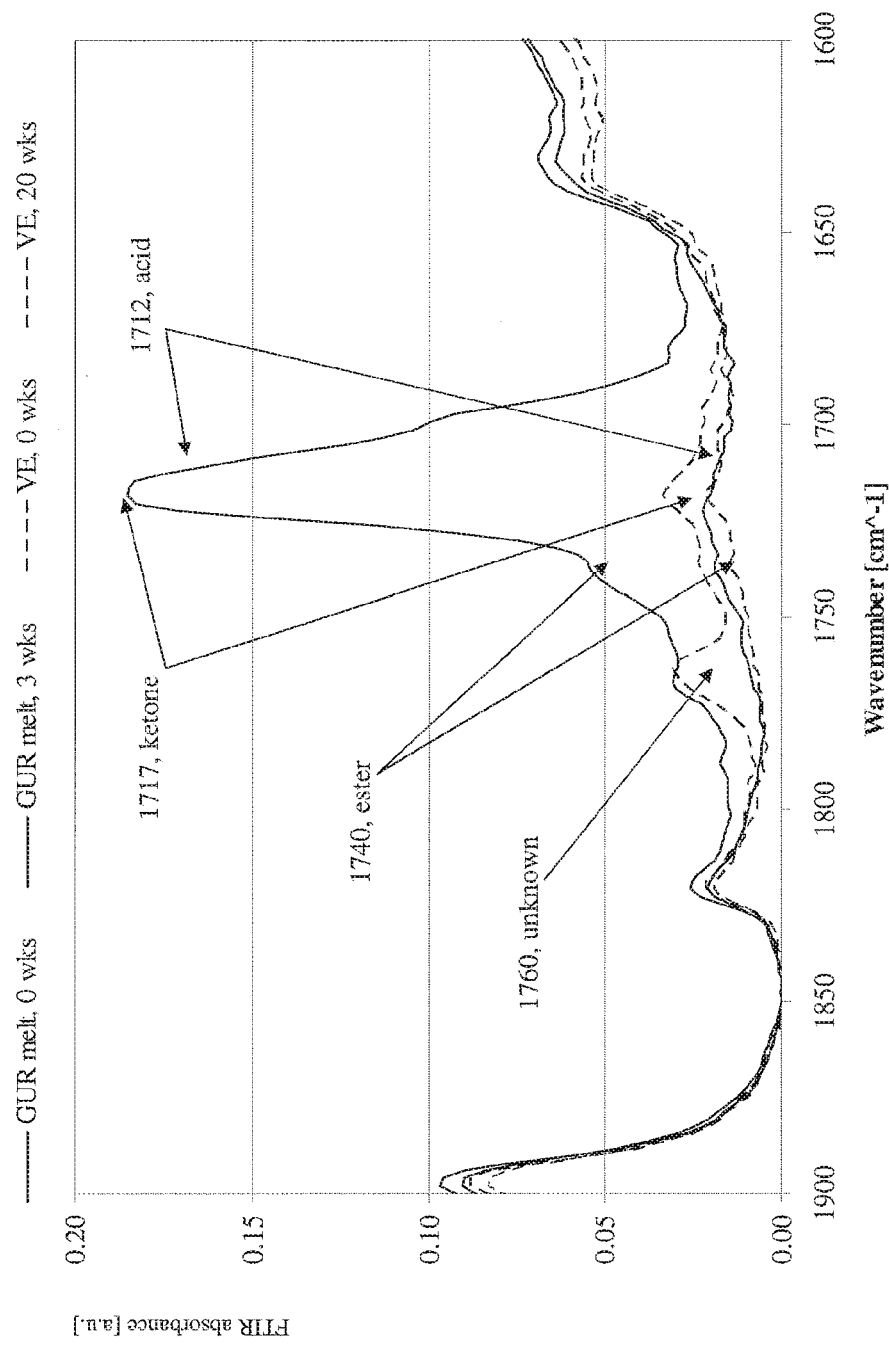
FIG. 10A shows a representative plot of an FT-IR.

FIG. 10A shows FT-IR spectra of the GUR melt and VE sample prior to aging and after aging as indicated therein.

FT-IR spectra exhibited significant baseline curvature in the region of the carbonyl oxidation peak (1650-1850 cm-1), leading to negative values for the oxidation peak area in some samples and therefore some negative OI values. While these negative values can be generally considered too low for use as absolute values for assessing oxidation of articles produced from blends of UHMWPE and one or more antioxidants, the raw spectra from formulations tested here revealed development of absorbance peaks between 1650-1850 cm-1, leading to increased peak area in this region and indicating a change in oxidation relative to the initial state.

The primary observed carbonyl peak corresponds to ketone groups at 1717 $cm^{-1}$, with possible contribution from acid groups at 1712 $cm^{-1}$, and a minor peak or shoulder corresponding to esters at 1740 $cm^{-1}$. An additional absorbance peak at 1760 $cm^{-1}$ was observed in this region for all formulations, which is unidentified in the literature to our knowledge. Control formulations exhibited this peak as a shoulder on the much stronger nearby ketone/ester/acid peak, whereas the AO-stabilized formulations showed a distinct peak here with absorbance similar to that of the ketone/ester/acid peak. The appearance of this distinct peak in AO-stabilized formulations that show very low increase in ketone/ester/acid absorbance may suggest the presence of another oxidation product, with reaction pathway possibly substantially different than that of ketones, esters, and acids. The functional group(s) responsible for absorption at 1760 $cm^{-1}$ may be part of the UHMWPE chain, AO molecule, or both.

OI increased in two distinct patterns: a rapid initial rise with a subsequent plateau, (FIG. 4) and a slow, linear increase with time (FIG. 5, detail view of FIG. 4). This observed plateau results from saturation of the FT-IR signal at the carbonyl peak, rather than a true chemical change in the material. Rapidly oxidizing samples include both CUR controls and one antioxidant containing sample, the octatriene sample, and all of these formulations showed saturation of the carbonyl peak between 1650 and 1850 cm-1 at some point during aging. Control sample, GUR melt, saturated after 10 weeks, while control sample, GUR and octatriene sample saturated after only 7 weeks with much higher OI values, confirming that the remelt process can increase oxidative stability. All other samples exhibited low levels of oxidation and did not saturate the carbonyl peak for the full 20 weeks of aging (FIG. 6 through FIG. 10).

Further analysis of the OI data was accomplished by calculating a linear rate of oxidation (OI-rate) by linear regression of oxidation index as a function of time in weeks, wth units [OI/wk]. The OI-rate data is shown below in Table 7.

TABLE 7

| Sample | OI/Wk |
| --- | --- |
| GUR melt | 0.913947 |
| GUR | 1.734224 |
| VE | 0.006005 |
| g-T | 0.004909 |
| Trolox | 0.005973 |
| Trolox/VE (0.1/0.1) | 0.006113 |
| Chromanol | 0.007202 |
| L. gallate | 0.005385 |
| O. gallate | 0.003213 |
| P. Gallate | 0.003182 |
| Curcumin | 0.008201 |
| Resveratrol | 0.009015 |
| Catechin | 0.008209 |
| Chlorogenic acid | 0.011216 |

TABLE 7-continued

| Sample | OI/Wk |
| --- | --- |
| Tannic acid | 0.003977 |
| Gallic acid | 0.016069 |
| Ellagic acid | 0.029275 |
| Bilberry (0.2) | 0.008924 |
| Rutin | 0.008571 |
| Hesperidin | 0.010005 |
| Naringin | 0.009257 |
| Doverphos (DP) | 0.011564 |
| DP/VE (0.05/0.15) | 0.004014 |
| DP/VE (0.10/0.10) | 0.006341 |
| DP/VE (0.15/0.05) | 0.004677 |
| DP/VE (0.20/0.20) | 0.003903 |
| DP/L. gal (0.1/0.1) | 0.002113 |
| a-lipoic acid | 0.00777 |
| Genox 0.156 | 0.012451 |
| VC | 0.006664 |
| Octatriene | 1.502996 |
| Irg (0.2) | 0.00266 |

Figure 11:
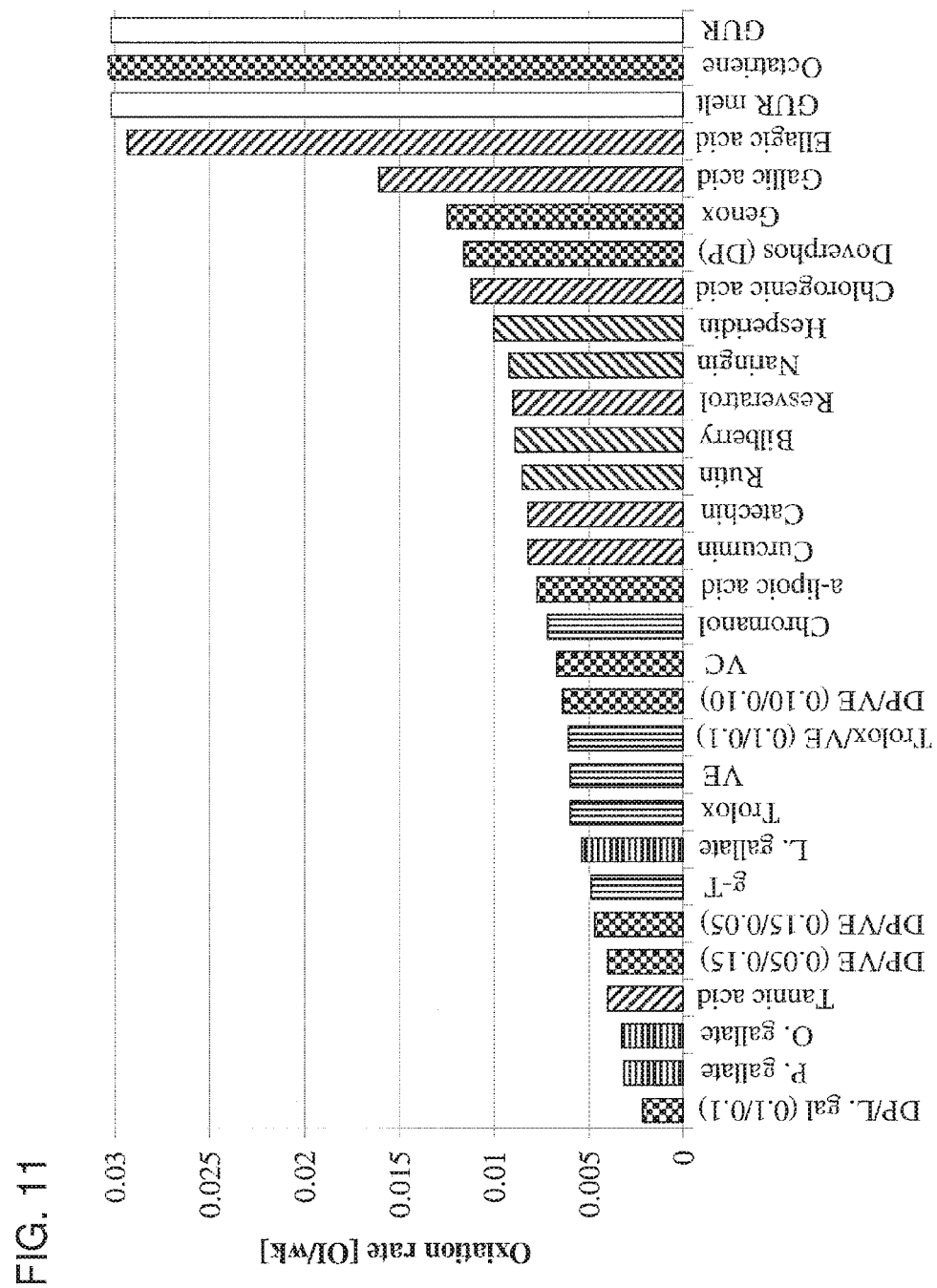
FIG. 11 shows a graph of OI-rate of samples including a blend of UHMWPE and a variety of one or more antioxidants.

This data is graphically represented in FIG. 11 with shading corresponding to antioxidant groups shown in Table 1. The results in FIG. 11 show the oxidation rate [OI/wk] values in order of increasing oxidation rate and rapidly oxidizing formulations (right) were truncated but with oxidation rates displayed numerically.

The plateau regions associated with FT-IR saturation in rapidly oxidizing samples were excluded. Rapidly oxidizing samples were clear outliers, with OI-rates on the order of 1 OI/wk while slower oxidizing samples exhibited OI-rates on the order of about 0.01 OI/wk. The octatriene sample is the only antioxidant containing sample to show high OI-rate, which may be attributed to its structure. Octatriene is the only 1° antioxidant without hydroxyl groups which are functional groups thought to facilitate stabilization of alkyl radicals. Even the Genox® sample, with just one hydroxyl group and no aryl stabilization, and Doverphos®, a 2° antioxidant exhibited OI-rates similar to those of simple phenolic antioxidants chlorogenic, gallic, and ellagic acid.

Oxidation rate values were plotted as a function of initial oxidation induction time as shown in FIG. 12. Oxidation rates (OI-rate) of rapidly oxidizing samples e.g. GUR, GUR melt and octatriene were off-scale as shown in FIG. 11, and fall well under 1 minute oxidation induction time (OIT).

As has been alluded to previously, the development of a crosslinked and stabilized UHMWPE component involves balancing the competing effects of radiation crosslinking and AO free radical scavenger activity. It would be advantageous to provide a method for rapidly differentiating higher performing antioxidant and UHMWPE blends in terms of high degree of wear resistance and oxidative stability without resorting to long-term mechanical wear resistance and oxidation testing. In one embodiment a hybrid parameter referred to as a "Performance Factor" (PF) can be calculated. Two potential PF calculations are provided for the data obtained from the samples tested, both using crosslink density as a surrogate for wear rate, and with either OIT or 1/OI-rate as a measure of oxidative stability.

The PFs defined here effectively ratio the sample's crosslink density to its propensity to oxidize, therefore a low crosslink density and poorly oxidation-stabilized material would yield a low PF value, whereas a high crosslink density and highly oxidation resistant samples yield a high PF.

Figure 13:
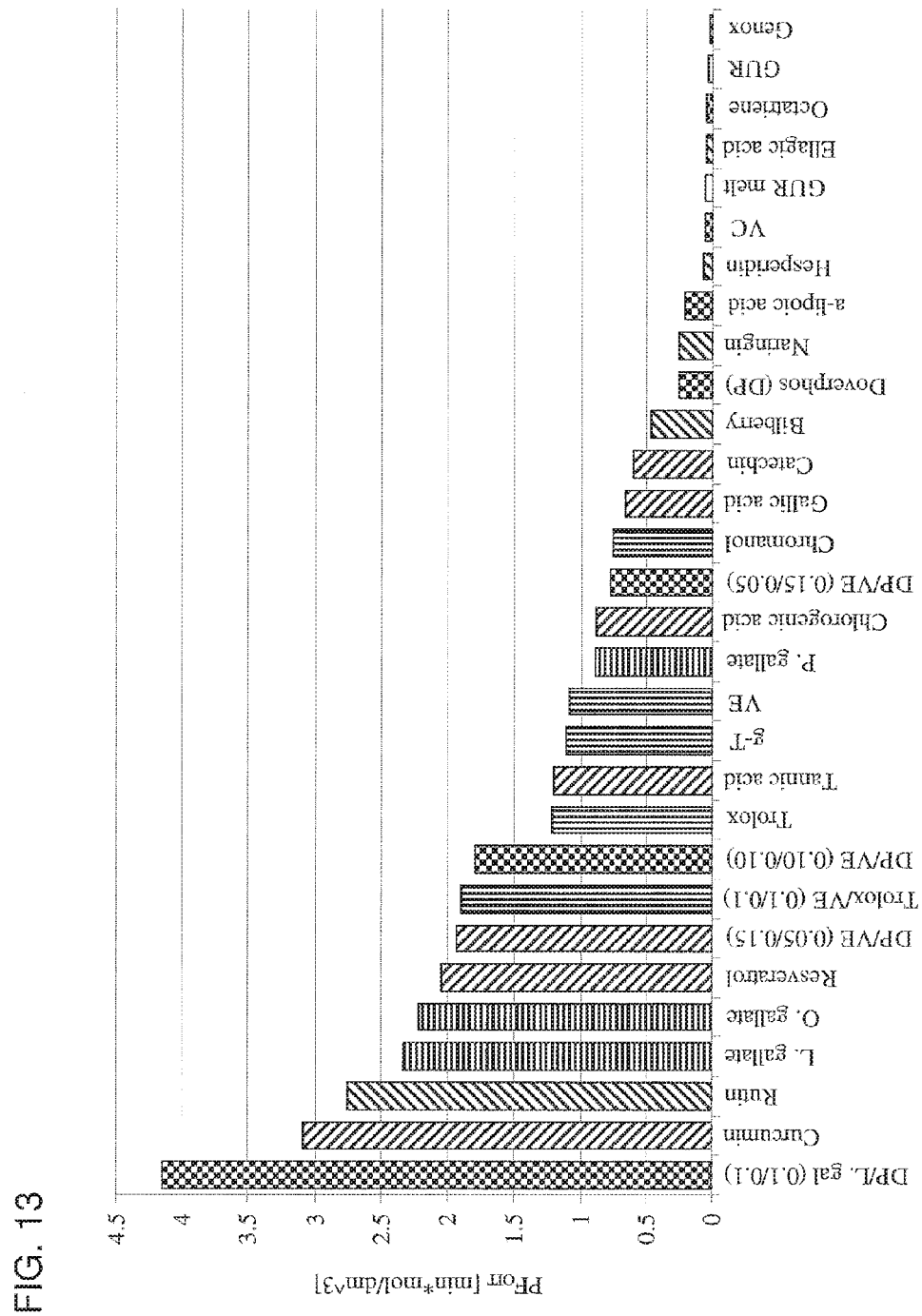
FIG. 13 shows a graph of Performance Factor OIT of samples including a blend of UHMWPE and a variety of one or more antioxidants.
Figure 14:
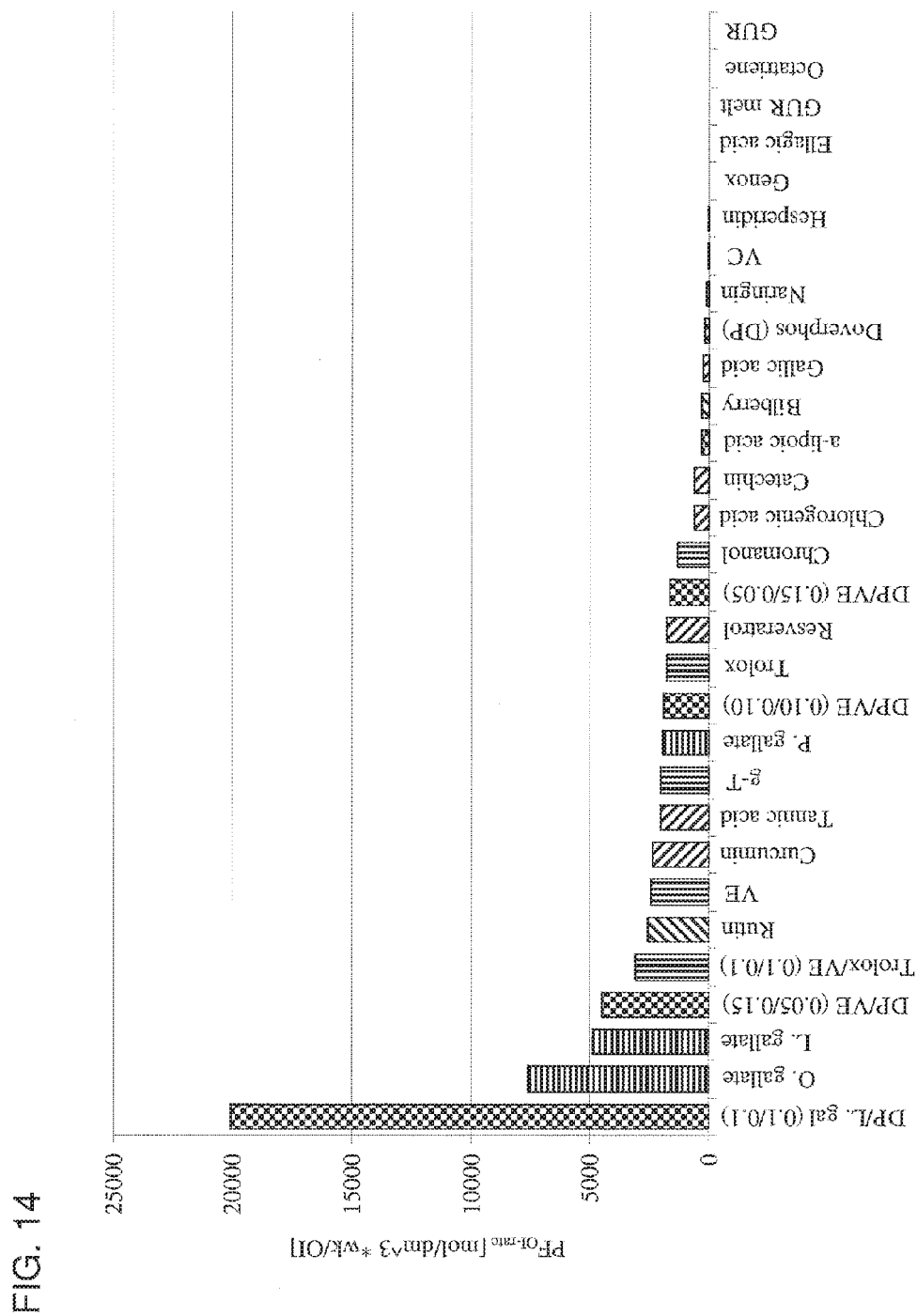
FIG. 14 shows a graph of Performance Factor OI-rate of samples including a blend of UHMWPE and a variety of one or more antioxidants.

Performance factor $PF_{OIT}$ was calculated for each sample by calculating the product of OIT and crosslink density (XLD) for the particular sample and performance factor $PF_{OI\text{-}rate}$ was calculated for each sample by calculating the product of the crosslink density (XLD) and the inverse of OI-rate. Table 8 below presents the calculated $PF_{OIT}$ and $PF_{OI\text{-}rate}$ and FIG. 13 and FIG. 14 present the results in graphical form.

TABLE 8

| Sample | $PF_{OIT}$<br>XLD*OIT<br>[min*mol/dm^3] | $PF_{OI\text{-}rate}$<br>XLD/OI-rate<br>[mol/dm^3*wk/OI] |
|---|---|---|
| GUR melt | 0.056967 | 0.320952 |
| GUR | 0.035506 | 0.132624 |
| VE | 1.086807 | 2446.777 |
| g-T | 1.106101 | 2030.326 |
| Trolox | 1.212986 | 1803.043 |
| Trolox/VE (0.1/0.1) | 1.897346 | 3061.923 |
| Chromanol | 0.754592 | 1361.131 |
| L. gallate | 2.340416 | 4881.407 |
| O. gallate | 2.21854 | 7615.864 |
| P. Gallate | 0.890191 | 1996.437 |
| Curcumin | 3.088843 | 2391.082 |
| Resveratrol | 2.042051 | 1767.036 |
| Catechin | 0.604612 | 620.8816 |
| Chlorogenic acid | 0.874351 | 642.5399 |
| Tannic acid | 1.202825 | 2079.601 |
| Gallic acid | 0.663352 | 283.7735 |
| Ellagic acid | 0.049898 | 8.881367 |
| Bilberry (0.2) | 0.462661 | 296.9657 |
| Rutin | 2.757382 | 2535.795 |
| Hesperidin | 0.072422 | 46.64398 |
| Naringin | 0.250879 | 156.6459 |
| Doverphos (DP) | 0.255162 | 160.8401 |
| DPNE (0.05/0.15) | 1.932161 | 4499.684 |
| DP/VE (0.10/0.10) | 1.794485 | 1947.142 |
| DP/VE (0.15/0.05) | 0.776293 | 1684.118 |
| DP/VE (0.20/0.20) | 2.929196 | 6904.413 |
| DP/L. gal (0.1/0.1) | 4.151084 | 20050.99 |
| a-lipoic acid | 0.207238 | 337.6181 |
| Genox 0.156 | 0.028164 | 14.45654 |
| VC | 0.059187 | 69.52464 |
| Octatriene | 0.042884 | 0.199601 |
| Irg (0.2) | 3.456327 | 10935.64 |

While the present approach has been described in detail with reference to the foregoing embodiments, other changes and modifications may still be made without departing from the spirit or scope of what is disclosed. It is understood that the methods, compositions and polymers described herein are not to be limited by the embodiments described herein. Indeed, the true measure of the scope of the present approach is defined by the appended claims including the full range of equivalents given to each element of each claim.

The invention claimed is:

1. An orthopedic implant, comprising:
  a consolidated and crosslinked UHMWPE blend, the UHMWPE blend comprising:
    a homogeneous blend of UHMWPE resin,
    6-hydroxy-2,5,7,8-tetramethylchroman-2-carboxylic acid, and
    a primary antioxidant chosen from lauryl gallate, octyl gallate, propyl gallate, curcumin, resveratrol, rutin, vitamin E, gamma-tocopherol, 2,2,5,7,8-penta-methyl-6-chromamol, catechin, chlorogenic acid, tannic acid, gallic acid, ellagic acid, bilberry, hesperidin, naringin, E-4-hydroxy nonenal, vitamin C, 2,6-dimethyl-2,4,6-octratriene, and pentaerythritol tetrakis (3-(3,5-di-tert-4-hydroxyphenyl)propionate),
  wherein a combined concentration of the 6-hydroxy-2,5,7,8-tetramethylchroman-2-carboxylic acid and the primary antioxidant prior to crosslinking is about 0.05% to about 5% by weight of the UHMWPE blend.

2. The orthopedic implant of claim 1, wherein the consolidated and crosslinked UHMWPE blend has a crosslink density, an oxidation index rate, and an oxidation induction time measure by the offset method, and the product of the crosslink density and oxidation induction time is greater than 1.5.

3. The orthopedic implant of claim 1, wherein the product of the crosslink density and the inverse of the oxidation index rate of the consolidated and crosslinked UHMWPE blend is greater than 2500.

4. The orthopedic implant of claim 1, wherein the consolidated and crosslinked UHMWPE blend has an oxidation induction time as measured by the offset method of greater than 15 minutes.

5. The orthopedic implant of claim 1, wherein the consolidated and crosslinked UHMWPE blend has an oxidation index rate of less than 0.006 OI/week.

6. The orthopedic implant of claim 1, wherein the primary antioxidant is sufficient to react directly with free peroxy radicals (—OO.) at a higher rate than directly with hydroperoxides (—OOH).

7. The orthopedic implant of claim 1, wherein the 6-hydroxy-2,5,7,8-tetramethylchroman-2-carboxylic acid is sufficient to react directly with hydroperoxides (—OOH) at a higher rate than directly with free peroxy radicals (—OO.).

8. The orthopedic implant of claim 1, wherein the combined concentration of the primary antioxidant and the 6-hydroxy-2,5,7,8-tetramethylchroman-2-carboxylic acid prior to cross linking the UHMWPE blend is about 0.05% to about 2% by weight of UHMWPE blend.

9. The orthopedic implant of claim 1, wherein the combined concentration of the primary antioxidant and the 6-hydroxy-2,5,7,8-tetramethylchroman-2-carboxylic acid prior to cross linking the UHMWPE blend is about 0.05% to about 1% by weight of the UHMWPE blend.

10. The orthopedic implant of claim 1, wherein the primary antioxidant is vitamin E, gamma-tocopherol, or 2,2,5,7,8-penta-methyl-6-chromanol.

11. The orthopedic implant of claim 1, wherein the primary antioxidant is vitamin E.

12. A method of making the orthopedic implant of claim 1, the method comprising:
  mixing UHMWPE resin with a primary antioxidant and a 6-hydroxy-2,5,7,8-tetramethylchroman-2-carboxylic acid to obtain a homogeneous blend, wherein the primary antioxidant is chosen from lauryl gallate, octyl gallate, octyl gallate, propyl gallate, curcumin, resveratrol, rutin, vitamin E, gamma-tocopheol, 2,2,5,7,8-penta-methyl-6-chromamol, catechin, chlorogenic acid, tannic acid, gallic acid, ellagic acid, bilberry, hesperidin, naringin, E-4-hydroxy nonenal, vitamin C, 2,6-dimethyl-2,4,6-octratriene, and pentaerythritol tetrakis (3(3,5-di-tert-4-hydroxyphenyl)propionate), wherein the combined concentration of the primary antioxidant and the 6-hydroxy-2,5,7,8-etramethylchroman-2-carboxylic acid prior to the crosslinking of the UHMWPE blend is about 0.05% to about 5% by weight of the UHMWPE blend;
  consolidating the blend; and
  irradiating the consolidated blend to crosslink the consolidated blend.

13. The method of claim 12, wherein the mixing comprises
  mixing the UHMWPE resin with the primary antioxidant, and
  mixing the UHMWPE resin with the 6-hydroxy-2,5,7,8-tetramethylchroman-2-carboxylic acid.

14. The method of claim 12, wherein the mixing comprises mixing the UHMWPE resin with vitamin E and 6-hydroxy-2,5,7,8-tetramethylchroman-2-carboxylic acid.

15. The method of claim 12, wherein the irradiating the consolidated blend to crosslink the consolidated blend comprises irradiating the consolidated blend with at least one of electron beam radiation, gamma radiation, and x-ray radiation.

16. The method of claim 15, wherein a total crosslinking irradiation dose is substantially between about 50 kGy and about 1000 kGy.

17. The method of claim 12, wherein the irradiation treatment is provided by e-beam radiation at a dose rate of at least 1 MegaGrey per hour.

18. The method of claim 12, wherein the irradiation treatment is provided by e-beam radiation at a dose rate of at least 18 MegaGrey per hour.

19. The method of claim 12, wherein the method further includes preheating the consolidated blend to a preheat temperature below the melting point of the consolidated blend.

20. A method of making an orthopedic implant, the method comprising:
mixing UHMWPE resin with 6-hydroxy-2,5,7,8-tetramethylchroman-2-carboxylic acid and a primary antioxidant chosen from lauryl gallate, octyl gallate, propyl gallate, curcumin, resveratrol, rutin, vitamin E, gamma-tocopherol, 2,2,5,7,8-penta-methyl-6-chromamol, catechin, chlorogenic acid, tannic acid, gallic acid, ellagic acid, bilberry, hesperidin, naringin, E-4-hydroxy nonenal, vitamin C, 2,6-dimethyl-2,4,6-octratriene, and 6-hydroxy-2,5,7,8-tetramethylchroman-2-carboxylic acid to obtain a homogeneous blend, wherein the combined concentration of the primary antioxidant and the 6-hydroxy-2,5,7,8-tetramethylchroman-2-carboxylic acid prior to the crosslinking of the UHMWPE blend is about 0.05% to about 5% by weight of the UHMWPE blend;
consolidating the blend; and
irradiating the consolidated blend to crosslink the consolidated blend;
wherein the orthopedic implant comprises the crosslinked consolidated blend, the crosslinked consolidated blend comprising
a homogeneous blend of UHMWPE resin,
the 6-hydroxy-2,5,7,8-tetramethylchroman-2-carboxylic acid, and
the primary antioxidant.

* * * * *

UNITED STATES PATENT AND TRADEMARK OFFICE
CERTIFICATE OF CORRECTION

PATENT NO.       : 9,707,316 B2
APPLICATION NO.  : 15/149583
DATED            : July 18, 2017
INVENTOR(S)      : Thomas et al.

It is certified that error appears in the above-identified patent and that said Letters Patent is hereby corrected as shown below:

In the Claims

In Column 34, Line 20, in Claim 6, delete "(-OO.)" and insert --(-OO·)-- therefor In Column 34, Line 25, in Claim 7, delete "(-OO.)." and insert --(-OO·).-- therefor In Column 34, Line 47, in Claim 12, after "gallate,", delete "octyl gallate,"

In Column 34, Line 53, in Claim 12, delete "(3(3,5-di-tert-4-hydroxyphenyl)propionate)," and insert --(3-(3,5-di-tert-4-hydroxyphenyl)propionate),-- therefor In Column 34, Line 55-56, in Claim 12, delete "6-hydroxy-2,5,7,8-etramethylchroman-2-carboxylic" and insert --6-hydroxy-2,5,7,8-tetramethylchroman-2-carboxylic-- therefor Signed and Sealed this
Tenth Day of April, 2018

Andrei Iancu
*Director of the United States Patent and Trademark Office*